(12) United States Patent
Uhlmann et al.

(10) Patent No.: US 7,241,882 B2
(45) Date of Patent: Jul. 10, 2007

(54) POLYAMIDE NUCLEIC ACID DERIVATIVES, AND AGENTS, AND PROCESSES FOR PREPARING THEM

(75) Inventors: Eugen Uhlmann, Glashuetten (DE); Gerhard Breipohl, Frankfurt (DE); David William Will, Kriftel (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 376 days.

(21) Appl. No.: 10/863,999

(22) Filed: Jun. 9, 2004

(65) Prior Publication Data

US 2004/0265885 A1 Dec. 30, 2004

Related U.S. Application Data

(62) Division of application No. 09/835,370, filed on Apr. 17, 2001, now Pat. No. 6,777,544.

(30) Foreign Application Priority Data

Apr. 18, 2000 (DE) ............................... 100 19 136

(51) Int. Cl.
C07H 21/00 (2006.01)
C07H 21/02 (2006.01)
C07H 21/04 (2006.01)
C12Q 1/68 (2006.01)

(52) U.S. Cl. .................. 536/25.3; 536/23.1; 536/24.3; 435/6

(58) Field of Classification Search .................. 435/6; 536/23.1, 24.3, 25.3
See application file for complete search history.

(56) References Cited

U.S. PATENT DOCUMENTS

| 5,874,553 A | | 2/1999 | Peyman et al. | |
| 6,043,352 A | * | 3/2000 | Manoharan et al. | ....... 536/24.2 |
| 6,046,306 A | * | 4/2000 | Breipohl et al. | ............ 630/322 |

FOREIGN PATENT DOCUMENTS

| CA | 2217377 | 4/1998 |
| DE | 19508923 A1 | 9/1996 |
| DE | 19640974 A1 | 4/1998 |
| WO | WO 92/20702 | 11/1992 |
| WO | WO9611205 | 4/1996 |
| WO | WO 99/33867 | 7/1999 |
| WO | WO9933867 | 7/1999 |

OTHER PUBLICATIONS

Uhlmann et al Nucleosides & Nucleotides vol. 16 (5&6) pp. 603-608 1997.*
Weiler et al. (NAR vol. 25 No. 14 pp. 2792-2799 pp. 1997.*
Praseuth et al., "Triple Helix Formation and the Antigene Strategy for Sequence-Specific Control of Gene Expression", Biochem. Biophys. Acta 1489(1):181-206, Dec. 10, 1999.

Mischiati et al., "Interaction of the Human NF-κβ p. 52 Transcription Factor with DNA-PNA Hybrids Mimicking the NF-κβ Binding Sites of the Human Immunodeficiency Virus Type 1 Promoter", J. Biol. Chem. 274(46):33114-33122, Nov. 12, 1999.
Cole-Strauss et al., "Correction of the Mutation Responsible for Sickle Cell Anemia by an RNA-DNA Oligonucleotide", Science 273:1386-1389, Sep. 6, 1996.
Ørum et al., "Labeling of PNA", Peptide Nucleic Acids: Protocols and Applications, pp. 81-86, 1999.
Lohse et al., "Fluorescein-Conjugated Lysine Monomers for Solid Phase Synthesis of Fluorescent Peptides and PNA Oligomers", Bioconjugate Chem. 8(4):503-509, Jul./Aug. 1997.
Wiitung et al., "Phospholipid Membrane Permeability of Peptide Nucleic Acid", FEBS Lett. 365(1):27-29, May 22, 1995.
Koch et al., "PNA-Peptide Chimerae", Tetrahedron Lett. 36(38):6933-6936, Sep. 18, 1995.
Egholm et al., "Peptide Nucleic Acids (PNA): Oligonucleotide Analogues with an Achiral Peptide Backbone", J. Am. Chem. Soc. 114(5):1895-1897, Feb. 26, 1992.
Nielsen et al., Appendix, "Peptide Nucleic Acids—Protocols and Applications", Horizon Scientific Press, pp. 253-255, 1999.
Falkiewicz, B., "Peptide Nucleic Acids and Their Structural Modifications", Acta Biochim. Polonica 46(3):509-529, 1999.
Sosnowski et al., "Rapid Determination of Single Base Mismatch Mutations in DNA Hybrids by Direct Electric Field Control", Proc. Natl. Acad. Sci. USA 94(4):1119-1123, Feb. 1997.
Hung et al., "Comparison of Fluorescence Energy Transfer Primers with Different Donor-Acceptor Dye Combinations", Analytical Biochemistry 255(1):32-38, Jan. 1, 1998.
Tarrason et al., "Intracellular Distribution of Digoxigenin-Labeled Phosphorothioate Oligonucleotides", Methods in Enzymology 313:257-268, 1999.
Matthes et al., "Telomerase Protein Rather than its RNA is the Target of Phosphorothioate-Modified Oligonucleotides", Nucleic Acids Research 27(4):1152-1158, Feb. 15, 1999.
Hayashi et al., "In Vivo Transfer of Gene and Oligodeoxynucleotides into Skin of Fetal Rats by Incubation in Amniotic Fluid", Gene Therapy 3(10):878-885, Oct. 1996.
Just et al., "Flow Cytometric Detection of EBV (EBER snRNA) Using Peptide Nucleic Acid Probes", Journal of Virological Methods 73(2):163-174, Aug. 1998.
Strother et al., "Synthesis and Characterization of DNA-Modified Silicon (111) Surfaces", J. Am. Chem. 122(6)1205-1209, Feb. 16, 2000.
Pirrung, M., "Spatially Addressable Combinatorial Libraries", Chem. Rev. 97(2):473-488, Mar./Apr. 1997.

(Continued)

Primary Examiner—Jezia Riley

(57) ABSTRACT

The present invention relates to PNA derivatives which carry, at the N terminus of the PNA backbone, a phosphoryl radical. The phosphoryl radical can be, for example, a phosphate radical, or a substituted phosphoryl radical, with substituted phosphoryl derivatives carrying, where appropriate, one or more labeling groups, groups for crosslinking, groups which promote intracellular uptake, or groups which increase the binding affinity of the PNA derivative for nucleic acids. The invention furthermore relates to a process for preparing the abovementioned PNA derivatives and to their use as pharmaceuticals and diagnostic agents.

7 Claims, 12 Drawing Sheets

OTHER PUBLICATIONS

Wang et al., "Peptide Nucleic Acid Probes for Sequence-Specific DNA Biosensors", *J. Am. Chem. Soc.* 118(33):7667-7670, Aug. 21, 1996.

Will et al., "The Synthesis of Polyamide Nucleic Acids Using a Novel Monomethoxytrityl Protecting-Group Strategy", *Tetrahedron* 51(44):12069-12082, Oct. 30, 1995.

Breipohl et al., "Novel Synthetic Routes to PNA Monomers and PNA-DNA Linker Molecules", *Tetrahedron* 53(43):14671-14686, Oct. 27, 1997.

Sonveaux, E., "The Organic Chemistry Underlying DNA Synthesis", *Bioorganic Chemistry* 14(3):274-325, Sep. 1986.

Beaucage et al., "The Functionalization of Oligonucleotides Via Phosphoramidite Derivatives", *Tetrahedron* 49(10):1925-1963, Mar. 5, 1993.

Ravin, L., "Preformulation", *Remington's Pharmaceutical Sciences*, Mack Publishing Company, Easton, PA, pp. 1409-1423, 1985.

Niemeyer et al., "DNA Microarrays", *Angew. Chem. Int. Ed.* 38(19)2865-2869, 1999.

PCT Search Report; PCT/EP 01/04027 (Nov. 26, 2001).

Uhlmann et al., Nucleosides & Nucleotides, vol. 16, (5&6), 1997, pp. 603-608.

Weiler et al., (NAR vol. 25, No. 14, 1997, pp. 2792-2799.

Nielsen et al., "Peptide Nucleic Acids—Protocols and Applications", Horizon Specific Press, 1999, pp. 2-3.

Nielsen et al., "Sequence-Selective Recognition of DNA by Strand Displacement with a Thymine-Substituted Polyamide", *Science* 254:1497-1500, Dec. 6, 1991.

Egholm et al., "PNA Hybridizes to Complementary Olgionucleotides Obeying the Watson-Crick Hydrogen-Bonding Rules", *Nature* 365(6446):566-568, Oct. 7, 1993.

Nielsen et al., "Peptide Nucleic Acid (PNA) A DNA Mimic with a Peptide Backbone", *Bioconjugate Chem.* 5(1):3-7, Jan./Feb. 1994.

Uhlmann et al., "PNA: Synthetic Polyamide Nucleic Acids with Unusual Binding Properties", *Angew. Chem. Int. Ed.* 37(20):2796-2823, Nov. 2, 1998.

Greiner et la., "Influence of the Type of Junction in DNA-3'-Peptide Nucleic Acid (PNA) Chimeras on Their Binding Affinity to DNA and RNA", *Helvetica Chimica Acta* 82(12):2151-2159, 1999.

Nielsen et al., "Peptide Nucleic Acids—Protocols and Applications", *Horizon Scientific Press*, pp. 2-3, 1999.

Uhlmann et al., "Antisense Oligonucleotides: A New Therapeutic Principle", *Chemical Reviews* 90(4):543-584, Jun. 1990.

Larsen et al., "Antisense Properties of Peptide Nucleic Acid", *Biochim. Biophys. Acta* 1489(1):159-166, Dec. 10, 1999.

Weiner et al., "Liposomes as a Drug Delivery System", *Drug Develop. and Ind. Pharm.* 15(10):1523-1554, 1989.

\* cited by examiner

Fluorescein (Amide)

Fluorescein (Thiourea)

Tetrachlorofluorescein

Hexachlorofluorescein

Acridin

DNP

Biotin

Fluorescein
(Thiourea)

Cholesterol

Cy3

Cy5

Spacer-9

Spacer-18

TAMRA

Phosphorylating reagent 1

Phosphorylating reagent 2

Fluorescein phosphoramidit 3 (monofunctional)

Fluorescein phosphoramidit 4 (bifunctional)

Biotin phosphoramidit 5 (monofunctional)

Biotin phosphoramidit 6 (bifunctional)

C16-phosphorylating reagent 7

Spacer-9 phosphoramidit 8

Spacer-18 phosphoramidit 9

Cyanin-3 phosphoramidit 10

Cyanin-5 phosphoramidit 11

Aminomodifier-5
phosphoramidit 12

Aminomodifier-C6
phosphoramidit 13

E

F

SEQUENCE LISTING

<160> NUMBER OF SEQ ID NOS: 64

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 1
gcgtttgctc ttcttcttgc g                                          21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 2
acacccaatt ctgaaaatgg                                            20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 3
aggtccctgt tcgggcgcca                                            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 4
gcggggctcc atggggtcg                                             20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 5

```
cagctgcaac ccagc                                                      15

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 6
tattccgtca t                                                          11

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 7
ttccgtcatc gctcctcagg gg                                              22

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 8
ggctgccatg gtccc                                                      15

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 9
ggctgctgga gcggggcaca c                                               21

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 10
aacgttgagg ggcat                                                      15

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:  nucleotide
```

-continued base sequence of PNA derivatives that bind to
    viral and cellular targets

<400> SEQUENCE: 11
gtgccggggt cttcgggc                                                18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:  nucleotide
    base sequence of PNA derivatives that bind to
    viral and cellular targets

<400> SEQUENCE: 12
cgagaacatc atcgtgg                                                 17

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:  nucleotide
    base sequence of PNA derivatives that bind to
    viral and cellular targets

<400> SEQUENCE: 13
ggagaacatc atggtcgaaa g                                            21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:  nucleotide
    base sequence of PNA derivatives that bind to
    viral and cellular targets

<400> SEQUENCE: 14
cccgagaaca tcatggtcga ag                                           22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  nucleotide
    base sequence of PNA derivatives that bind to
    viral and cellular targets

<400> SEQUENCE: 15
ggggaaagcc cggcaagggg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  nucleotide
    base sequence of PNA derivatives that bind to
    viral and cellular targets

<400> SEQUENCE: 16
cacccgcctt ggcctcccac                                              20

<210> SEQ ID NO 17

```
<211> LENGTH: 18
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 17
gggactccgg cgcagcgc                                                  18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 18
ggcaaacttt cttttcctcc                                                20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 19
gggaaggagg aggatgagg                                                 19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 20
ggcagtcatc cagcttcgga g                                              21

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 21
tctcccagcg tgcgccat                                                  18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 22
```

-continued

```
gcgctgatag acatccatg                                              19

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 23
ggaggcccga cc                                                     12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 24
ggtttcggag gc                                                     12

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 25
tggtggaggt ag                                                     12

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 26
gcatggtgga gg                                                     12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 27
ttggcatggt gg                                                     12

<210> SEQ ID NO 28
<211> LENGTH: 12
<212> TYPE: DNA
<213> ORGANISM: Artificial Sequence
<220> FEATURE:
```

-continued

```
<223> OTHER INFORMATION: Description of Artificial Sequence:  nucleotide
      base sequence of PNA derivatives that bind to
      viral and cellular targets

<400> SEQUENCE: 28
gcctgggacc ac                                                          12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 29
cagcctggga cc                                                          12

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 30
tgcagcctgg ga                                                          12

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 31
gtgcagcctg gg                                                          12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 32
ggtgcagcct gg                                                          12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 33
atgggtgcag cc                                                          12
```

```
<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 34
ggcttgaaga tg                                                            12

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 35
gcagcccccg ca                                                            12

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 36
gcagcagccc cc                                                            12

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 37
tcccgcctgt gacatgcatt                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 38
gttctcgctg gtgagtttca                                                    20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets
```

```
<400> SEQUENCE: 39
gcgtgcctcc tcactggc                                                     18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 40
gcagtaagca tccatatc                                                     18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 41
gcccaagctg gcatccgtca                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 42
cccccaccac ttcccctctc                                                   20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 43
ctcccccacc acttcccctc                                                   20

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 44
gctgggagcc atagcgagg                                                    19

<210> SEQ ID NO 45
<211> LENGTH: 21
<212> TYPE: DNA
<213> ORGANISM: Artificial Sequence
```

```
<220> FEATURE:
<223> OTHER INFORMATION: Description of Artificial Sequence:  nucleotide
      base sequence of PNA derivatives that bind to
      viral and cellular targets

<400> SEQUENCE: 45
actgctgcct cttgtctcag g                                               21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 46
caatcaatga cttcaagagt tc                                              22

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 47
gcggcggaaa agccatcg                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 48
gtgtcggggt ctccgggc                                                   18

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 49
cacgttgagg ggcat                                                      15

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 50
gtcttccata gttactca                                                   18
```

```
<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 51
gatcaggcgt gcctcaaa                                                       18

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 52
gatggagggc ggcatggcgg g                                                   21

<210> SEQ ID NO 53
<211> LENGTH: 4
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 53 aact                                                                       4

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 54
acatcatggt cg                                                             12

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 55
ccacgatgat gt                                                             12

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets
```

<400> SEQUENCE: 56
gagccatgta tagtgac                                                                                    17

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 57
tcggtttgag atctgg                                                                                     16

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 58
tattccgtca t                                                                                          11

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 59
actgatgtag tc                                                                                         12

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 60
gctgatgtag tc                                                                                         12

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence:  nucleotide
      base sequence of PNA derivatives that bind to
      viral and cellular targets

<400> SEQUENCE: 61
ggtatgggat at                                                                                         12

<210> SEQ ID NO 62
<211> LENGTH: 12
<212> TYPE: DNA

```
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 62
tgaaggaaga gg                                                          12

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 63
gttagggtta g                                                           11

<210> SEQ ID NO 64
<211> LENGTH: 8
<212> TYPE: DNA
<213> ORGANISM: Artificial Sequence
<220> FEATURE:
<223> OTHER INFORMATION: Description of Artificial Sequence: nucleotide
      base sequence of PNA derivatives that bind to
      viral and cellular targets

<400> SEQUENCE: 64 cccttcc                                                                 8
```

POLYAMIDE NUCLEIC ACID DERIVATIVES, AND AGENTS, AND PROCESSES FOR PREPARING THEM

BACKGROUND OF THE INVENTION

1. Field of the Invention

The present invention relates to N-terminally phosphorylated polyamide nucleic acid (PNA) derivatives having improved properties, to their use, and to agents and processes for preparing them.

2. Summary of the Related Art

Polyamide nucleic acids, also termed peptide nucleic acids (PNA), bind to complementary target sequences (DNA or RNA) with a higher affinity than do natural oligonucleotides and, furthermore, have the advantage, as compared with natural DNA, that they are very stable in serum. PNA were originally described as unnatural nucleic acid analogs in which the entire sugar-phosphate backbone is replaced with N-(2-aminoethyl)glycine units (M. Egholm et al. (1991) Science 254, 1497-1500; WO 92/20702; M. Egholm et al. Nature (1993) 365, 566-568; P. Nielsen, (1994) Bioconjugate Chem. 5, 3-7; E. Uhlmann et al. (1998) Angewandte Chemie Int. Ed. Engl. 37, 2796-2823). The bases employed in PNA are 1) nucleobases which occur naturally and are customary in nucleotide chemistry, 2) nucleobases which do not occur naturally, and 3) the prodrug forms of these two types of bases, that is, precursors which are only converted into the free base by biotransformation in the body.

PNAs have also been described in which not all the positions in the backbone carry base residues (Greiner et al. (1999) Helv. Chim Acta 82, 2151), and in which aminoethylglycine is replaced by more complex units (Uhlmann et al. (1998) Angewandte Chem. Int. Ed. 37, 2796; Falkiewicz (1999) Biochim. Pol., 46, 509-529).

The fact that the PNA backbone does not have any net charge is a feature of this class of substances that has far-reaching consequences. The fact that PNA binds to complementary DNA and RNA even at low salt concentration (see, for example, Peptide Nucleic Acids: Protocols and Applications; Peter E. Nielsen and Michael Egholm (Edit.) Horizon Scientific Press, 1999, page 3), with the Watson-Crick base pairing rules being obeyed, is ascribed to the neutral character of the PNA and the decrease in charge repulsion which is associated therewith. For this reason, PNA can, in principle, be used for numerous applications in which natural oligonucleotides or oligonucleotide derivatives would otherwise be employed. However, in addition to this, because of the unique binding properties, a large number of applications which are not possible with natural oligonucleotides also ensue (see, for example: Peptide Nucleic Acids: Protocols and Applications; Peter E. Nielsen and Michael Egholm (Edit.) Horizon Scientific Press, 1999). For example, a strand invasion of double-stranded DNA has been observed when using PNA, resulting in formation of triplex structures.

Typical examples of applications for PNA include its use for inhibiting gene expression by binding, in a sequence-specific manner, to cellular DNA or RNA. "Antisense agents" are short, single-stranded nucleic acid derivatives which bind, by means of Watson-Crick base pairing, to a complementary mRNA whose translation into the corresponding protein is to be inhibited (Uhlmann and Peyman (1990) Chem. Rev. 90, 543; Larsen et al. (1999) Biochem. Biophys. Acta 1489, 159). "Anti-gene agents" bind, by way of Hoogsteen base pairing, in the major groove of the DNA double helix with the formation of a triple helix, resulting in transcription of the genes being inhibited in a sequence-specific manner (Praseuth et al. (1999) Biochem. Biophys. Acta 1489, 181). Gene expression can also be specifically inhibited by so-called decoy oligomers, which mimic the regions for binding transcription factors. By treating with decoy agents, particular transcription factors can be captured in a sequence-specific manner and activation of transcription thereby prevented (Mischiati et al. (1999) J. Biol. Chem. 274, 33114). Another group of oligonucleotide derivatives which act intracellularly are the chimeraplasts. These are used for specific gene proof-reading (Cole-Strauss et al. (1996) Science 273, 1386-1389).

PNAs can, therefore, be used as pharmaceuticals and/or diagnostic agents or for producing pharmaceuticals and/or diagnostic agents. For example, after having been labeled with biotin, fluorescein, or other labels, PNA can be used as a specific hybridization probe for diagnostic purposes and in molecular biology.

Four methods have so far been described in the literature for introducing the labeling groups (Oerum et al. (1999), in Peptide Nucleic Acids: Protocols and Applications, pages 81-86; Lohse et al. (1997) Bioconjugate Chem. 8, 503). The first method is based on labeling the free (deprotected) PNA after it has been synthesized in solution. In this method, the amino terminus of the PNA is reacted with an activated carboxylic acid or an isothiocyanate. However, additional lysine residues are frequently introduced into the PNA, with these residues then being reacted with fluorescein isothiocyanate (FITC).

In the second method, the protected PNA is modified at its amino terminus with activated carboxylic acid derivatives or isothiocyanates while it is still on the solid phase. This method is only suitable for labeling groups which are stable under the conditions which pertain during deprotection of the PNA and during its cleavage from the support. The reactive reagents which are preferably used in both cases are isothiocyanates (P. Wittung et al., (1995) FEBS Lett. 375, 27) and activated carboxylic acids, such as N-hydroxysuccinimide esters (NHS) (Oerum et al., 1999). A disadvantage of the reaction using the NHS derivatives is that it is frequently only accomplished with poor yields. For this reason, 8-amino-3,6-dioxaoctanoic acid is frequently condensed, as a linker or spacer, between the PNA and the labeling group (Oerum et al., 1999). Both linkages are effected by way of amide bonds or thiourea bonds, which, as such, are, however, more likely to lead to insolubility. Alternatively, the carboxylic acids are caused to react using activators which are customary in peptide chemistry, such as HBTU, TBTU or HATU.

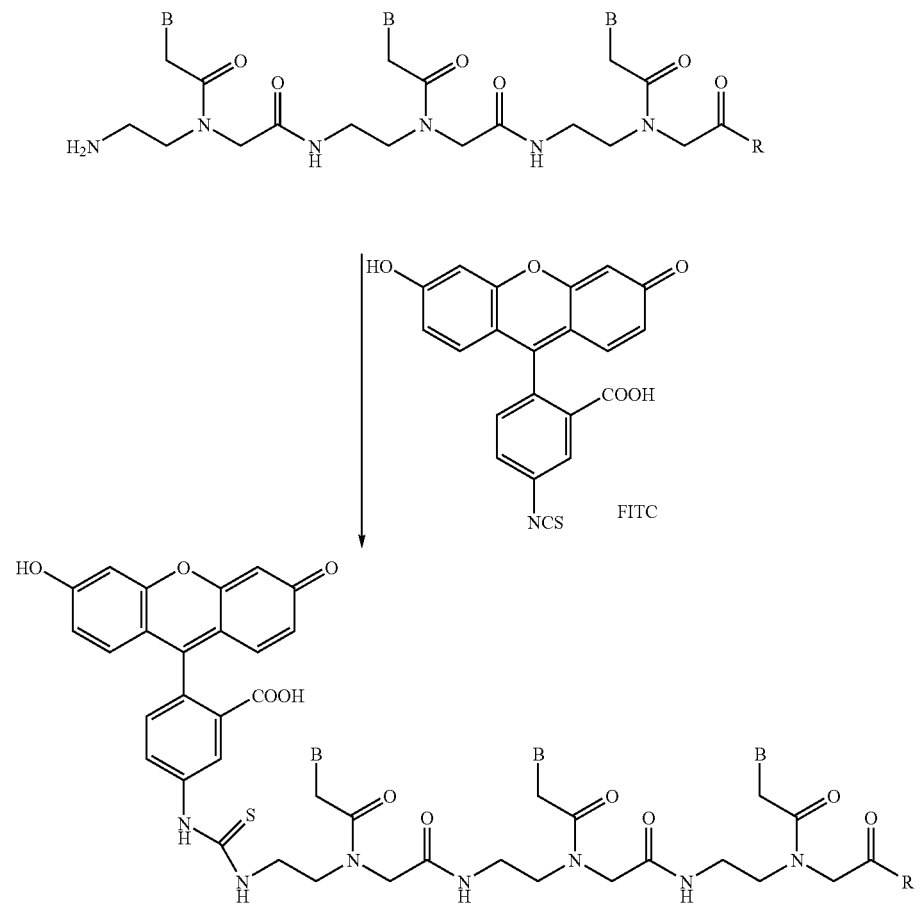

In a third method, shown generally above, fluorescein-conjugated monomers are used during the synthesis of the PNA on the solid phase, with the fluorescence labeling being effected by way of an amide bond (Lohse et al. (1997) Bioconjugate Chem. 8, 503), which once again leads to conjugates that are relatively difficult to dissolve.

A fourth method uses PNA peptide conjugates in which the peptide moiety forms a substrate for a protein kinase (Koch et al. (1995) Tetrahedron Lett. 36, 6933). In this way, therefore, it is not the PNA moiety which is modified; rather, the serine residue in the peptide segment is phosphorylated enzymatically. When this method is used, therefore, it is only possible to introduce radioactive phosphate, and not, for example, any fluorescein or biotin, into the peptide segment of the PNA-peptide conjugate. The general reaction is depicted as follows:

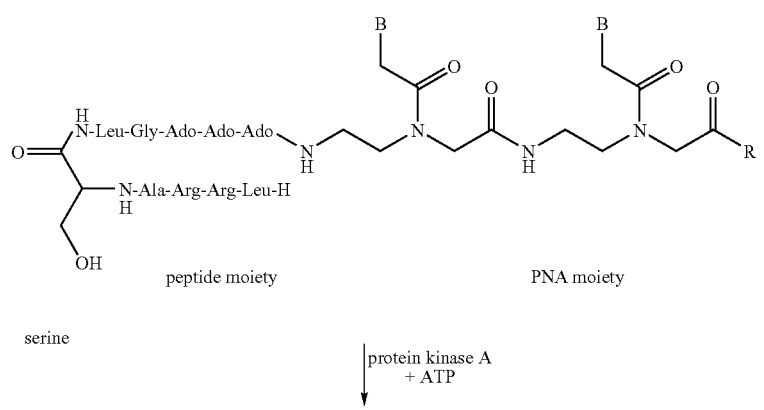

-continued

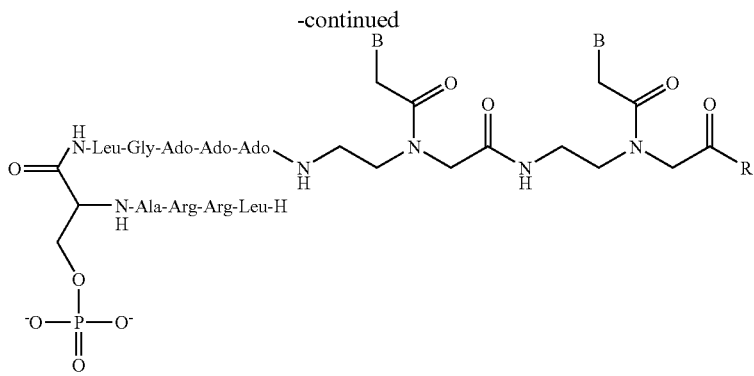

It is known that PNA tends to aggregate in aqueous solution. Thus, it is expected to aggregate under physiological conditions as well. Accordingly, PNA is poorly soluble in aqueous buffers and is thus unavailable for hybridizing to complementary sequences. Furthermore, PNA has a high affinity for various materials such as SEPHADEX® (from Pharmacia), BOND ELUT® (from Varian), or various HPLC chromatograph materials that are used in purifying oligomers. This means that PNA can frequently only be isolated in poor yields. It is therefore necessary to conjugate PNA with lysine or other positively charged amino acids (by way of the C terminus) (Egholm et al (1992) J. Am. Chem. Soc. 114, 1895). Guanine-rich PNA sequences have a very particular tendency to aggregate. For this reason, use of such PNA is generally discouraged (see "Guidelines for sequence design of PNA oligomers" in Peptide Nucleic Acids: Protocols and Applications (1999) pages 253-255). For example, relatively long fluorescein-labeled PNA oligomers are particularly difficult to dissolve, with the addition of an organic solvent and heating to 50° C. being recommended.

It is particularly difficult to purify the poorly soluble lipophilic PNA derivatives. Several peaks due to PNA aggregates are frequently detected in the HPLC. The technique of polyacrylamide (PAA) gel electrophoresis (or PAGE), which is frequently employed for purifying and separating nucleic acids, cannot be used for these PNA derivatives.

In the methods of derivatizing PNA which are described above, the labeling group is always introduced by forming an amide bond or a thioamide bond, with PNA derivatives being formed which are relatively difficult to dissolve. Poorly soluble PNA derivatives are formed, in particular, when lipophilic residues, such as fluorescein, are introduced. Furthermore, since the labeling reactions frequently proceed with poor yields, there is a need in the art to develop PNA derivatives that can be prepared in high yields, and which should exhibit advantageous properties, such as improved solubility, improved binding behavior, and better cellular uptake, and which, in addition, make it possible to use efficient methods for purifying the PNA oligomers.

DETAILED DESCRIPTION OF THE INVENTION

Figure 1A:
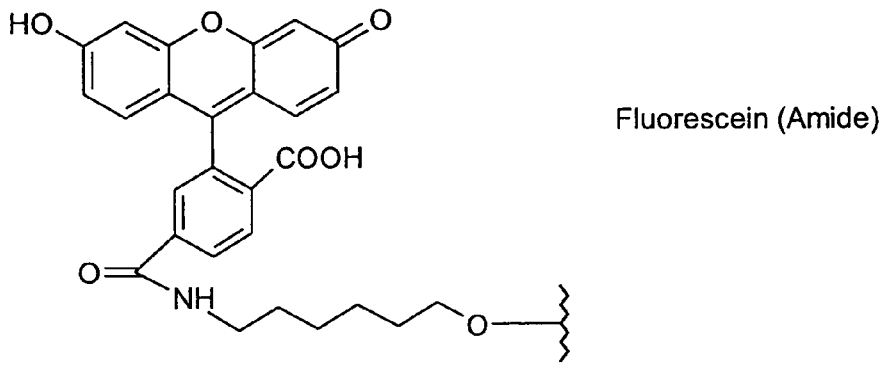
FIGS. 1a, 1b, 2b and 3b show examples of terminal Z radicals.
Figure 1A:
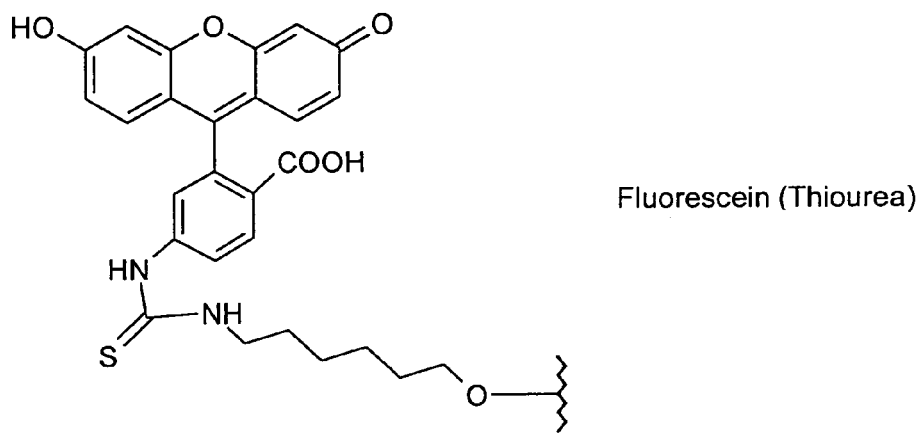
Figure 1A:
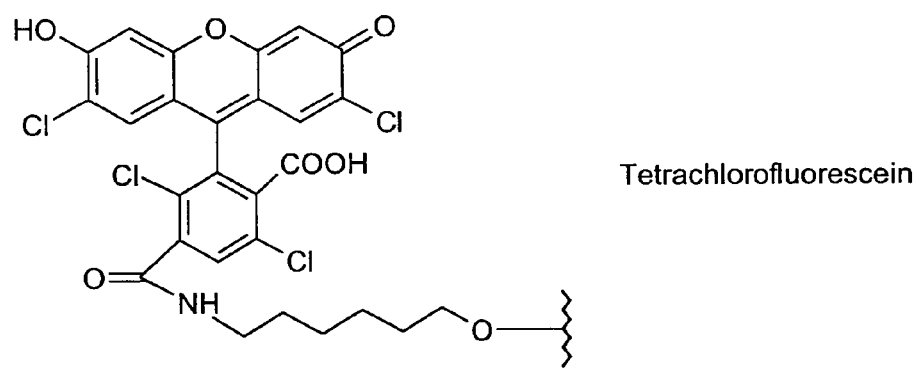
Figure 1A:
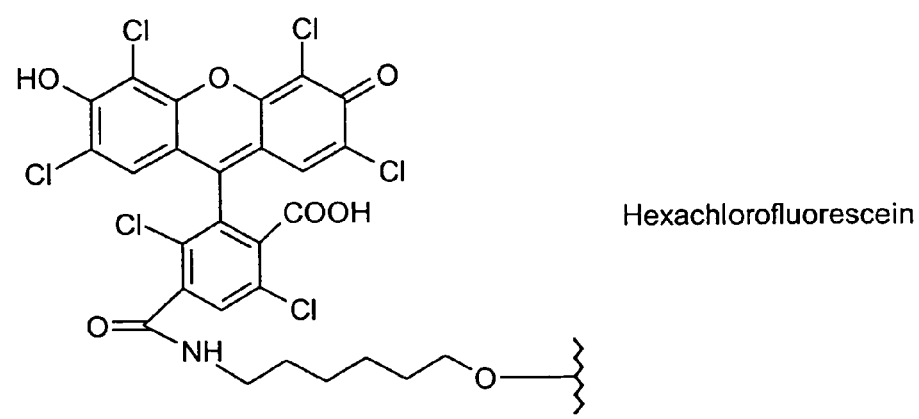
Figure 1B:
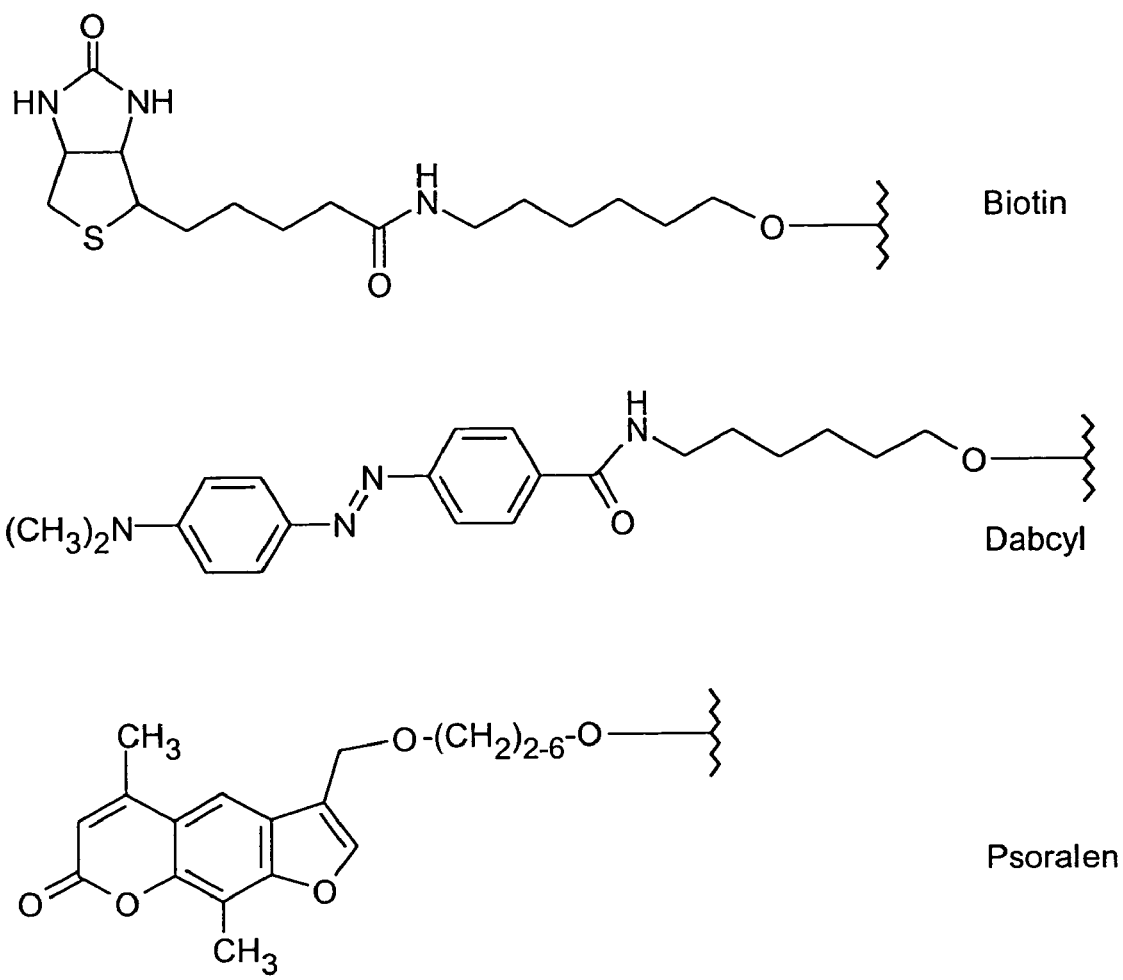
Figure 2A:
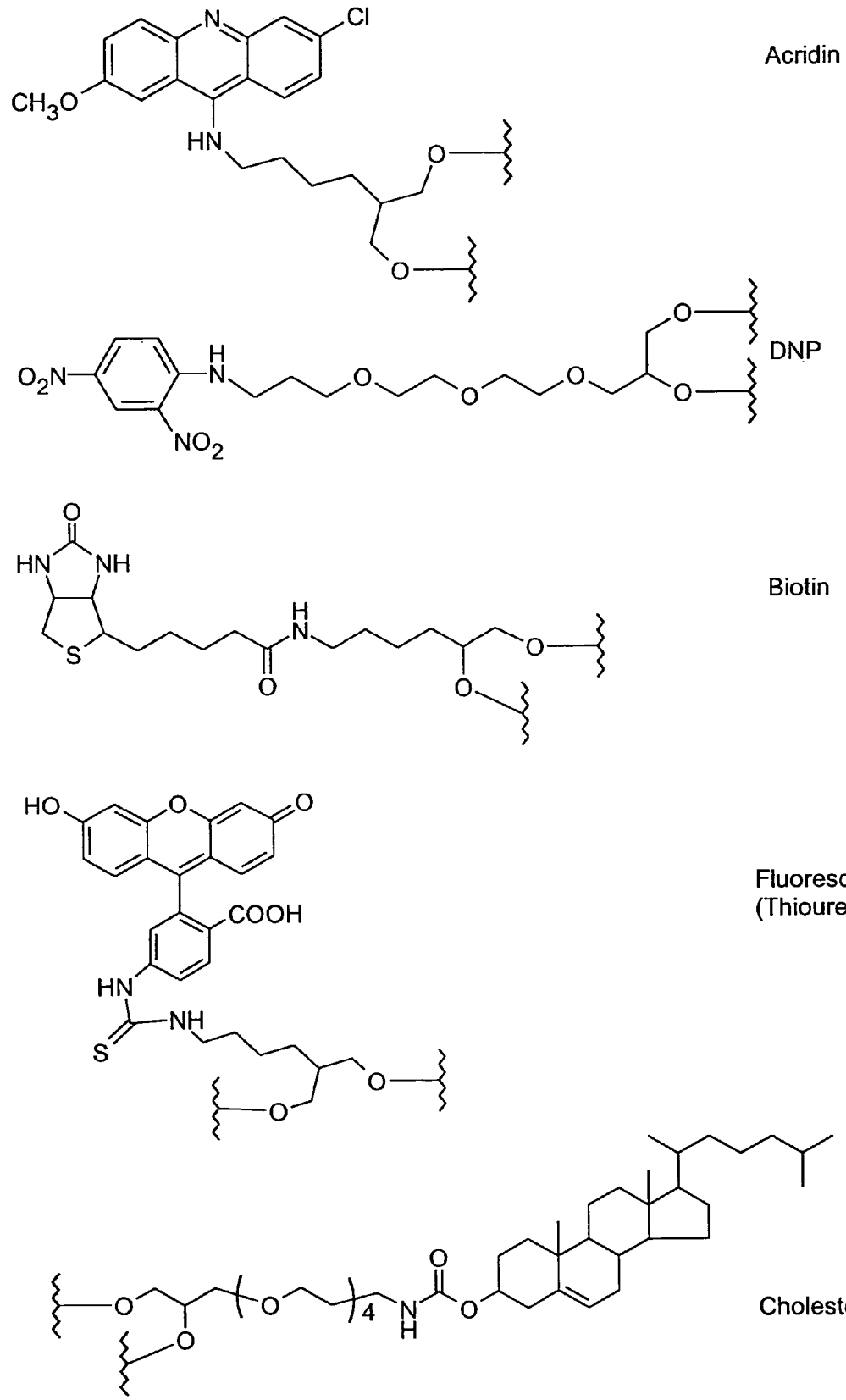
FIGS. 2a and 3a show examples of bridging X radicals.
Figure 2B:
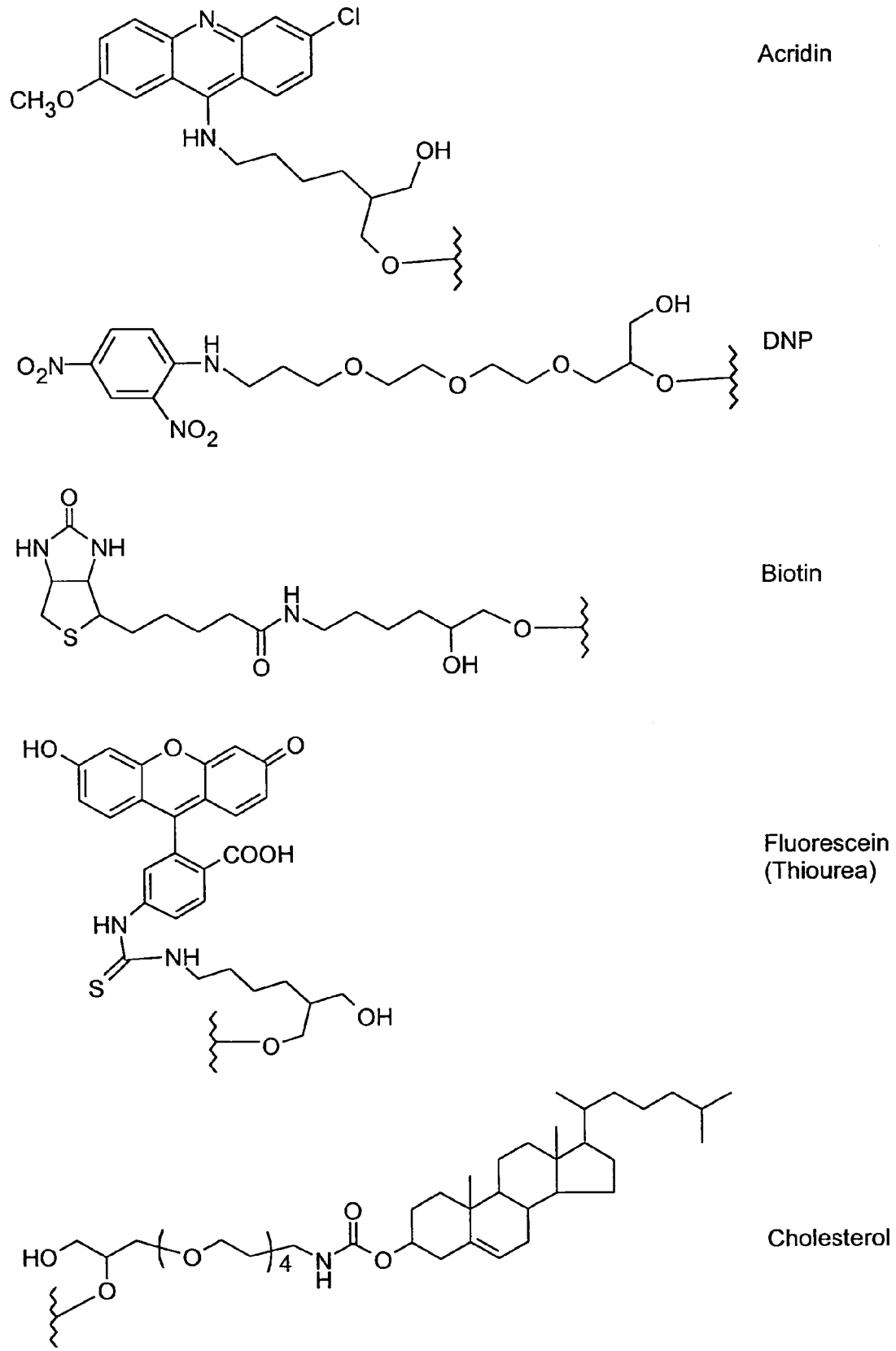
Figure 3A:
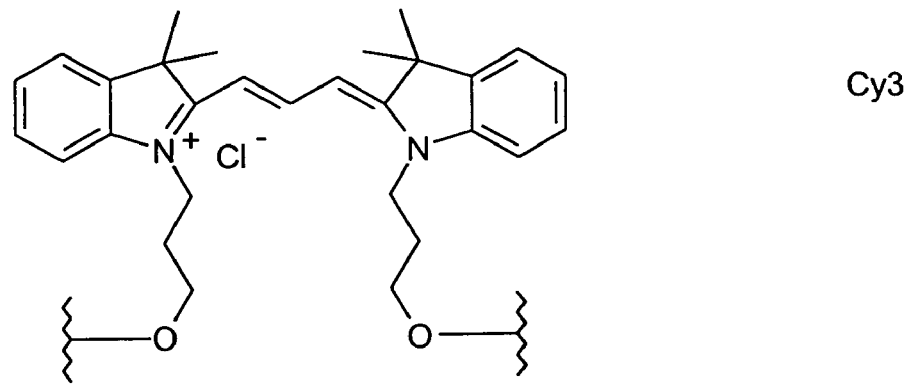
Figure 3A:
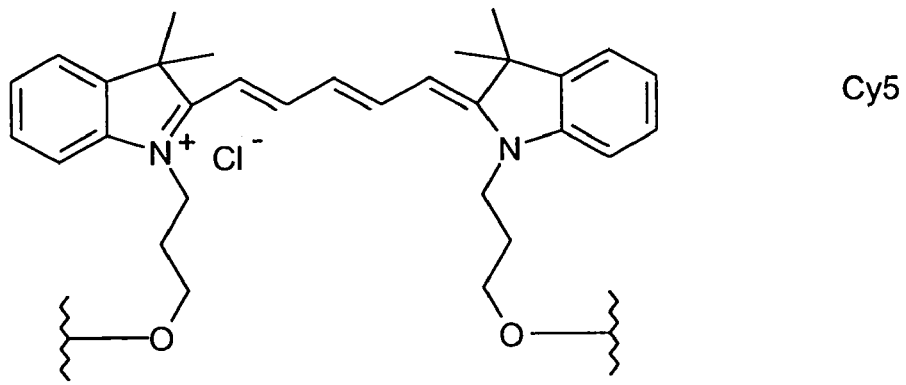
Figure 3A:
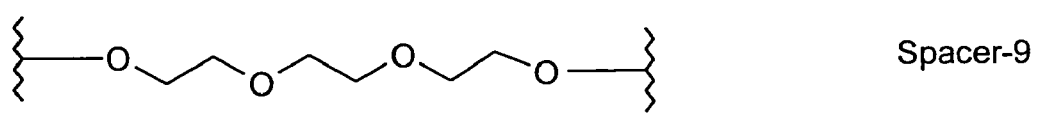
Figure 3A:
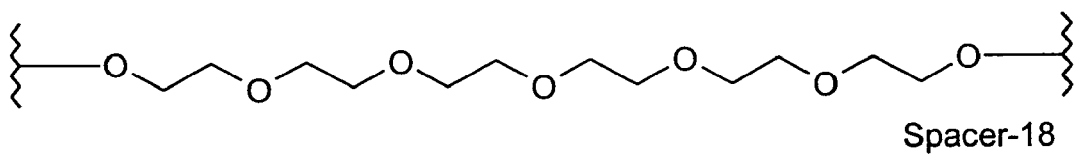
Figure 3A:
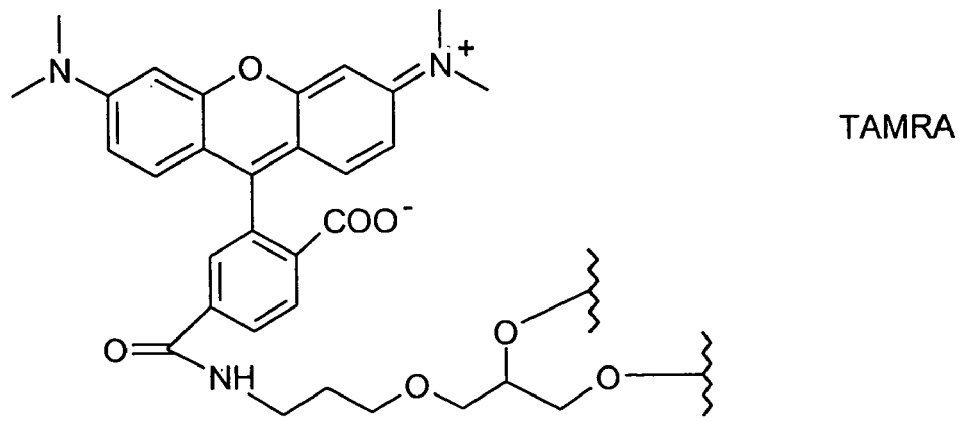
Figure 3B:
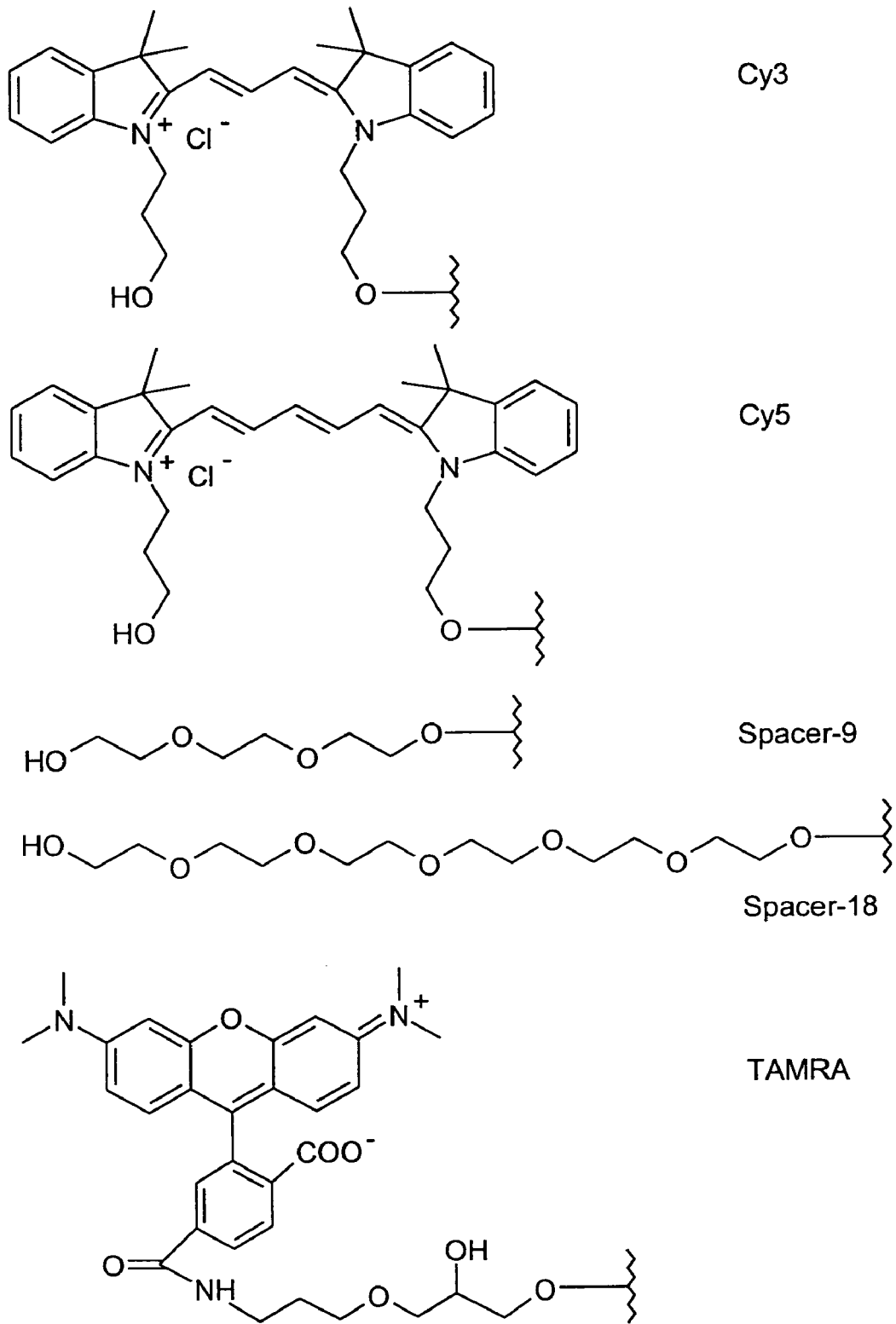

According to the invention, the needs of the art are achieved by providing PNA derivatives which carry one or more phosphoryl radicals at the N terminus of the PNA backbone. The invention provides PNA derivatives that are, among other things, thio derivatives, imino derivatives, and oxo derivatives. The PNA derivatives of the invention can have at least one of the phosphoryl radicals carry one or more deprotonatable groups, such as hydroxyl groups or mercapto groups. In these derivatives, the phosphoryl radicals are linked to the PNA backbone by way of an oxygen-phosphorus bond, sulfur-phosphorus bond, or nitrogen-phosphorus bond, either directly or by way of a spacer. The spacer can, but is not necessarily, an alkanoylamide, a poly(alkoxy)carboxamide, or an amino acid. Where appropriate, the spacer can carry a side chain at the α-C or β-C atom, where the side chain does not carry any phosphoryl radical.

Examples of phosphoryl radicals include, but are not limited to, phosphate, phosphonate, thiophosphate, phosphoamidate, and substituted phosphoryl radicals. The substituted phosphoryl radicals can carry, where appropriate, one or more labeling groups, groups for crosslinking, groups which promote intracellular uptake, or groups which increase the binding affinity of the PNA derivative for nucleic acids.

Labeling groups (labels) are understood as being groups which enable the chemical or biological activity of the PNA derivatives to be assessed qualitatively or quantitatively. Non-limiting examples are biotin and fluorescein. Crosslinking is understood as being the formation of intramolecular or intermolecular bonds between spatially adjacent functionalities. A non-limiting example of a group for crosslinking is the psoralen group.

In general, the invention relates to PNA derivatives of Formula I

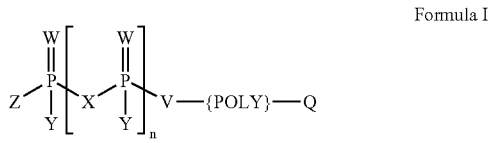

Formula I wherein

V is oxygen, sulfur, $NR_1$, $U-(CR_3R_4)_{u'}-C(O)-NH$, or $U-(CH_2CH_2O)_{u'}-CH_2-C(O)-NH$;

U is, independently of any other U, oxygen, sulfur, or NH;

u' is, independently of any other u', from 1 to 10, such as from 1 to 4, for example 1;

W is, independently of any other W, oxygen, sulfur, or $NR_1$;

Y is, independently of any other Y, hydroxyl, mercapto, oxyanion, thioate, or $NR_1R_2$;

$R_1$ and $R_2$ are, independently of each other, a radical consisting of hydrogen or $C_1$-$C_6$-alkyl;

$R_3$ and $R_4$ are, independently of each other, a radical consisting of hydrogen or $C_1$-$C_6$-alkyl, or the radical of an amino acid side chain;

X is, independently of any other X, $U-(C_2$-$C_{22}$-alkanediyl)-U, $U-(CH_2CH_2-O)_{u'}$, a labeling group, a group for crosslinking, a group which promotes intracellular uptake, or a group which increases the binding affinity of the PNA derivative for nucleic acids, for example a bifunctional fluorescein, rhodamine, TAMRA, biotin or a biotin derivative, pyrene, dinitrophenyl, cholesteryl, acridine, adamantyl, vitamin E, a cyanine dye, dabcyl, edans, lexitropsin, psoralen, BODIPY, ROX, R6G, or a digoxygenin radical;

Z is hydroxyl, mercapto, oxyanion, thioate, $NR_1R_2$, $C_1$-$C_{22}$-alkyl, $C_1$-$C_8$-arylalkyl, $C_1$-$C_{22}$-alkyl-U, $C_1$-$C_8$-arylalkyl-U, hydroxy-$C_1$-$C_{18}$-U, aminoalkyl-U or mercaptoalkyl-U, a group of the formula $R_9(CH_2CH_2-O)_m$, wherein $R_9$ is hydroxyl, amino or $C_1$-$C_{22}$-alkoxy, and m is from 1 to 100, for example from 2 to 10, a labeling group, a crosslinking group, a group which promotes intracellular uptake, or a group which increases the binding affinity of the PNA derivative for nucleic acids, for example a monofunctional or bifunctional fluorescein, rhodamine, TAMRA, biotin or biotin derivative, pyrene, dinitrophenyl, cholesteryl, acridine, adamantyl, vitamin E, a cyanine dye, dabcyl, edans, lexitropsin, psoralen, BODIPY, ROX, R6G, or a digoxygenin radical;

n is from 0 to 10, for example from 0 to 3;

Q is hydroxyl, amino, $NHR_7$, $NR_7R_8$, an amino acid derivative, or a peptide radical;

$R_7$ and $R_8$ are, independently of each other, $C_1$-$C_{18}$-alkyl or hydroxy-$C_1$-$C_{18}$-alkyl, with the proviso that at least one Y or Z radical is hydroxyl, mercapto, oxyanion, or thioate;

wherein {POLY} is described by Formula II

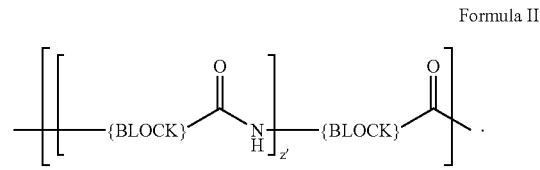

Formula II

The PNA backbone is consequently composed of z'+1 monomers, wherein {BLOCK} is, independently of any other {BLOCK}, a group selected from Formula IIIA,

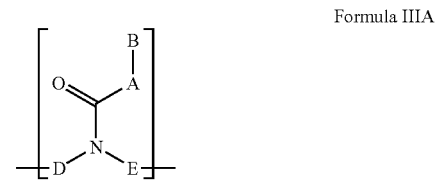

Formula IIIA

Formula IIIB (Greiner et al. (1999) Helv. Chim Acta 82, 2151),

Formula IIIB or Formulae IV A to IV G (Uhlmann et al. (1998) Angewandte Chem. Int. Ed. 37, 2796; Falkiewicz (1999) Biochim. Pol., 46, 509-529),

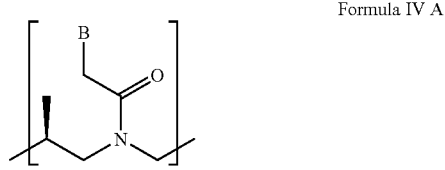

Formula IV A

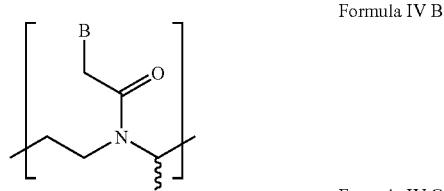

Formula IV B

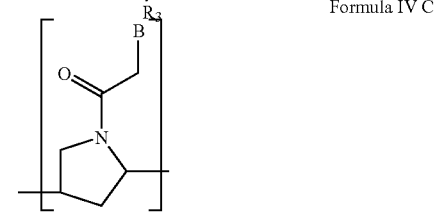

Formula IV C

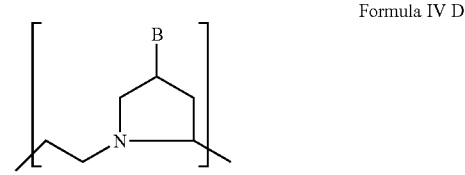

Formula IV D

-continued

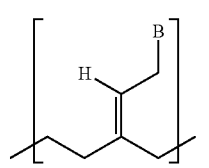

Formula IV E

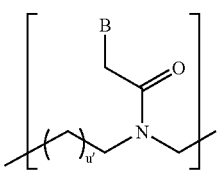

Formula IV F

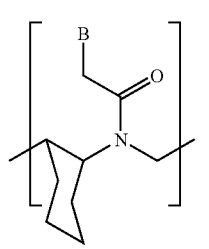

Formula IV G wherein each {BLOCK} building block can be different;
and wherein

A is, independently of any other A, a group $(CR_1R_2)_s$, wherein s is from 1 to 3, for example 1;

B is, independently of any other B, an aromatic radical, which can also possess heteroaromatic character, or hydrogen, hydroxyl or $C_1$-$C_{18}$-alkyl, or a nucleobase which occurs naturally, and is customary in nucleotide chemistry, or which does not occur naturally, or its prodrug form, wherein at least one B radical in Formula II is a nucleobase;

D is, independently of any other D, a group $(CR_3R_4)_t$, wherein t is from 2 to 10, such as from 2 to 4, for example 2, wherein $R_3$ and $R_4$ have the above-mentioned meaning, and two adjacent D radicals can also form a $C_5$-$C_8$-cycloalkyl ring;

E is, independently of any other E, a group $(CR_5R_6)_{u'}$, $R_5$ and $R_6$ are, independently of each other, a radical consisting of hydrogen or $C_1$-$C_6$-alkyl, such as hydrogen, or the radical of an amino acid side chain, wherein two adjacent $R_5$ and $R_6$ radicals can form a $C_5$- to $C_8$-cycloalkyl ring or a spiro compound;

z' is from 0 to 100, such as 1-20, for example 4-15; and wherein u', $R_1$, and $R_2$ are as defined above.

In addition, the invention relates to physiologically tolerated salts of the PNA derivatives of the Formula I. Physiologically tolerated salts are described, for example, in Remington's Pharmaceutical Science (1985) Mack Publishing Company, Easton, Pa., USA, page 1418. In embodiments, the salts are ammonium salts, trialkylammonium salts, alkali metal salts (such as sodium salts and potassium salts), and alkaline earth metal salts (such as magnesium salts and calcium salts). In embodiments, the salts are sodium salts.

It has been found, surprisingly, that a negative partial charge on the phosphoryl radical is sufficient to improve the properties of the compounds of Formula I. For example, whereas PNA itself does not migrate during PAA gel electrophoresis, the compounds of Formula I migrate to the anode. Since the phosphoryl radical is only introduced in the last cycle during the synthesis of the compounds of Formula I, it is only the compounds according to the invention which migrate in the electrical field during the PAA gel electrophoresis, while all the erroneous sequences and byproducts do not migrate and can consequently be separated off in an extremely simple manner.

The hydroxy or mercapto substituents of the phosphoryl radicals of the PNA derivatives according to the invention can be deprotonated in a pH range of from about 4.5 to about 14, such as from about 6.5 to about 12, for example from about 6.5 to about 9. The fact that the phosphoryl radicals can be ionized can advantageously be exploited for purifying the compounds of Formula I. On the one hand, the compounds of Formula I can be purified by electrophoresis, for example polyacrylamide gel electrophoresis (PAGE). On the other hand, it is also possible to purify them using anion exchangers. In the latter case, the desired products can be eluted by using a salt gradient, for example a sodium chloride gradient. They can also be eluted with a pH gradient. The PNA derivatives of Formula I according to the invention can be simply and efficiently purified using anion exchangers. It was found that the uncharged byproducts are not retarded on the anion exchanger, whereas the charged product adhered to the column. After washing with water, it was possible to isolate the desired product in pure form using acetic acid or a sodium chloride solution. The anion exchangers employed can be strong anion exchangers or mixed-mode phases, such as OASIS MAX® (Waters GmbH, Eschborn).

It was furthermore found that the compounds of Formula I according to the invention are, in general, more readily soluble in aqueous media than are the corresponding PNA oligomers which do not possess the phosphoryl radical. This is particularly apparent in the form of a greatly improved solubility in aqueous media in the case of the lipophilic derivatives, such as the fluorescein derivatives or the hexadecyl derivatives.

An additional surprising, positive effect which was found was that the introduction of a phosphoryl radical, for example as phosphate or in the form of a lipophilic derivatization (e.g. as a hexadecyl phosphodiester), increases the affinity of the PNA for complementary DNA or RNA. This effect was unexpected since the strong bonding of PNA to complementary DNA or RNA was attributed to the neutral character of the PNA and the reduced charge repulsion which was associated therewith (see, for example, Peptide Nucleic Acids: Protocols and Applications; Peter E. Nielsen and Michael Egholm (Edit.) Horizon Scientific Press, 1999, page 3).

In embodiments, biotin is introduced particularly efficiently by way of a phosphoryl radical. For example, when used as hybridization probes, the biotinylated PNA of Formula I (where X and/or Z=biotin radical) displayed better binding properties and fewer spurious, nonspecific background effects than did corresponding biotinylated DNA probes.

In contrast to the uncharged PNA, the PNA derivatives of Formula I according to the invention can also migrate in an electric field, thereby making it possible to microlocate them and concentrate them on immobilized complementary nucleic acid derivatives. In the case of polyanionic oligonucleotides, the use of an electrical field for microlocation and concentration has already been described for rapidly determining base mismatches (Sosnowski et al. (1997) Proc. Natl. Acad. Sci. U.S.A. 94, 1119).

The invention relates, in embodiments, to PNA derivatives in which A and E of Formula IIIA and/or Formula IIIB are $CH_2$. The invention furthermore relates, in embodiments, to PNA derivatives in which D substituents of Formula IIIA and/or Formula IIIB are $(CH_2)_2$. In embodiments, the invention relates to PNA derivatives of Formula I in which V and W are oxygen, and Y is hydroxyl or oxyanion.

Non-exclusive examples of natural bases are adenine, cytosine, 5-methylcytosine, guanine, thymine, and uracil. Non-exclusive examples of unnatural bases are purine, 2,6-diaminopurine, $N^4N^4$-ethanocytosine, $N^6N^6$-ethano-2,6-diaminopurine, 5-($C_3$-$C_6$)-alkynyluracil, 5-($C_3$-$C_6$)-alkynylcytosine, 5-(1-propargylamino)uracil, 5-(1-propargylamino)cytosine, phenoxazine, 9-aminoethoxyphenoxazine, 5-fluorouracil or pseudoisocytosine, 5-(hydroxymethyl)uracil, 5-aminouracil, pseudouracil, dihydrouracil, 5-($C_1$-$C_6$)-alkyluracil, 5-($C_1$-$C_6$)-alkylcytosine, 5-($C_2$-$C_6$)-alkenylcytosine, 5-fluorocytosine, 5-chlorouracil, 5-chlorocytosine, 5-bromouracil, 5-bromocytosine, 7-deazaadenine, 7-deazaguanine, 8-azapurine, and 7-deaza-7-substituted purines.

In embodiments, Q of Formula I is a hydroxyalkylamino radical. In embodiments, it is a hydroxyhexylamino radical, or a derivative of a natural or unnatural amino acid or of a peptide. Suitable peptides include those which optimize the organ distribution or the cellular location of the PNA, such as transportan, insulin-like growth factor, nuclear localization signals, or other carrier sequences (Larsen et al. (1999) Biochim. Biophys. Acta 159-166). The peptide can also be used as an affinity tag, like, for example, a $(His)_6$ chain.

The present invention enables the X and Z radicals of Formula I to be varied broadly (non-limiting examples are given in FIGS. 1a, 1b, 2a, 2b, 3a, and 3a), and thereby makes it possible to introduce different specific functional features into the PNA.

One embodiment of Z is a $C_1$- to $C_{22}$-alkyl radical. In other embodiments, Z is a $C_1$- to $C_{22}$-alkoxy radical, such as a $C_{16}$-alkoxy radical. In other embodiments, the radical is a hydroxy-($C_1$-$C_{18}$-alkoxy) radical, such as $HO(CH_2)_{3-12}O$. In other embodiments, the radical is an aminoalkoxy radical, such as a 6-aminohexoxy or 5-aminopentoxy radical. In other embodiments, the radical is of the Formula $R_9(CH_2CH_2—O)_m$, wherein $R_9$ is hydroxyl, amino, or $C_1$-$C_{22}$-alkoxy. In embodiments, it is hydroxyl. In embodiments, m is from 0 to 100, for example from 2 to 10. In embodiments, the radical is $HO(CH_2CH_2—O)_2$. In other embodiments, the radical is $HO(CH_2CH_2—O)_6$. In other embodiments, the radical is $H_2N—(CH_2CH_2—O)_2$. Other examples of Z include, but are not limited to, mercaptoalkoxy radicals, such as 6-mercaptohexyloxy.

In embodiments, Z comprises a fluorescent group, such as fluorescein, rhodamine, TAMRA, or a cyanine dye. Non-limiting examples of fluorescent groups are presented in FIGS. 1a to 3a. In embodiments, Z is biotin. In other embodiments, Z is Dabcyl, psoralen, acridine, DNP, cholesterol (see, for example, FIGS. 1b and 2b), BODIPY-, ROX- or R6G radicals (Su-Chun Hung et al. (1998) Analytical Biochemistry 255, 32-38), or digoxigenin (Tarrason et al., Methods in Enzyology (1999) Vol. 313, 257-268). In addition to these, Z can be a group consisting of a monofunctional or a bifunctional fluorescein, rhodamine, TAMRA, biotin, pyrene, dinitrophenyl, cholesteryl, acridine, adamantyl, vitamin E, cyanine dye, Dabcyl, Edans, lexitropsin, or psoralen radical. Monofunctional end groups are listed by way of non-exclusive example in FIGS. 1a, 1b, 2a and 3a, while bifunctional bridging groups are listed by way of non-exclusive example in FIGS. 2b and 3a. In another embodiment, n of Formula I is 0, i.e. the PNA moiety carries only one phosphate or phosphoryl radical.

In embodiments, X of Formula I is U—($C_2$-$C_{22}$-alkanediyl)—U, where U is defined above. In embodiments, X is O—($C_2$-$C_{22}$-alkanediyl)—O. In embodiments, X is O—$(CH_2)_{2-6}$—O. In other embodiments, X is a group of the Formula U—$(CH_2CH_2—O)_{u'}$, wherein u' is from 1 to 10. In embodiments, u' is from 1 to 6. In embodiments, U is oxygen. In other embodiments, X comprises a fluorescent group such as fluorescein, rhodamine, TAMRA, or a cyanine dye, for example Cy3® (from Amersham Pharmacia Biotech). Non-exclusive exemplary bifunctional groups can be found in FIGS. 2a and 3a. In embodiments, X is biotin. Other groups which are suitable for X include, but are not limited to, Dabcyl, psoralen, acridine, DNP, cholesterol, BODIPY, digoxigenin, ROX-, and R6G radicals.

The different radicals for X and Z in Formula I can fulfill different functions. For example, the fluorescein radicals have far-reaching applications in DNA sequencing and signal amplification or as markers for determining the cellular uptake of PNA. The cyanine dye radicals (Cy3® and Cy5®) give a substantially more intense and longer-lasting fluorescence signal than does fluorescein itself. The psoralen radical can be employed for crosslinking with complementary nucleic acids. The acridine radical can be an effective intercalator and can thereby augment the binding affinity of the PNA. Biotin, acridine, and psoralen derivatives can also be used, for example in antisense experiments. In addition, hexadecyloxy and cholesterol derivatives can be used, for example for increasing the ability of the PNA to traverse membranes. DNP-labeled compounds of Formula I can be detected using anti-DNP antibodies. Aminoalkoxy radicals can be used for coupling on other groups, for example lexitropsin (cf. Example 17; PNA-16). In a similar way, mercaptoalkoxy groups can also be used for further derivatization.

The invention furthermore relates to the use of the PNA derivatives of Formula I as pharmaceuticals. These pharmaceuticals can be used for preventing and/or treating diseases which are accompanied by the expression or overexpression of particular genes. The invention furthermore relates to the use of PNA derivatives of Formula I as diagnostic agents. These diagnostic agents can be used, among other things, for diagnosing diseases at an early stage.

When being employed as pharmaceuticals or diagnostic agents, the PNA derivatives of the Formula I can be used as antisense agents, anti-gene agents, decoy agents, and chimeraplast agents, depending on their sequence.

In embodiments, the PNA derivatives according to the invention are used for producing pharmaceuticals for treating diseases in which defined genes are the cause, or are involved, as a result of their overexpression.

These pharmaceuticals can, for example, be used for treating diseases which are provoked by viruses, for example by CMV, HIV, HSV-1, HSV-2, influenza, VSV, hepatitis B, or papilloma viruses, with the corresponding virus sequence being the target.

Antisense PNA derivatives according to the invention which are active against these targets have, for example, the following base sequences.

a) against CMV, for example

SEQ ID NO:1    5'-GCGTTTGCTCTTCTTCTTGCG-3' b) against HIV, for example

```
SEQ ID NO:2     5'-ACACCCAATTCTGAAAATGG-3'
SEQ ID NO:3     5'-AGGTCCCTGTTCGGGCGCCA-3'
``` c) against HSV-1, for example

```
SEQ ID NO:4     5'-GCGGGGCTCCATGGGGTCG-3'.
```

Such pharmaceuticals are also suitable, for example, for treating cancer. In this connection, it is possible to use sequences which are directed against targets which are responsible for the carcinogenesis or the growth of a cancer. For example, they can be used to inhibit telomerase (E. Matthes et al. (1999) Nucleic Acids Res. 27, 1152). Additional non-limiting examples of targets of this nature are:

1) Nuclear oncoproteins, such as, for example, c-myc, N-myc, c-myb, c-fos, c-fos/jun, PCNA, and p120;
2) Cytoplasmic/membrane-associated oncoproteins, such as, for example, EJ-ras, c-Ha-ras, N-ras, rrg, bcl-2, cdc-2, c-raf-1, c-mos, c-src, c-abl, and c-ets;
3) Cell receptors, such as, for example, EGF receptor, Her-2, c-erbA, VEGF receptor (KDR-1), retinoid receptors, protein kinase regulatory subunit, c-fms, Tie-2, c-raf-1 kinase, PKC-alpha, and protein kinase A (R1 alpha);
4) Cytokines, growth factors and extracellular matrix, such as, for example, CSF-1, IL-6, IL-1a, IL-1b, IL-2, IL4, IL-6, IL-8, bFGF, VEGF, myeloblastin, and fibronectin.

Antisense PNA derivatives which are active against such targets have, for example, the following base sequences:

a) against c-Ha-ras, for example

```
SEQ ID NO:5     5'-CAGCTGCAACCCAGC-3'
SEQ ID NO:6     5'-TATTCCGTCAT-3'
SEQ ID NO:7     5'-TTCCGTCATCGCTCCTCAGGGG-3'
``` b) bFGF, for example

```
SEQ ID NO:8         5'-GGCTGCCATGGTCCC-3'
``` c) c-myc, for example

```
SEQ ID NO:9     5'-GGCTGCTGGAGCGGGGCACAC-3'
SEQ ID NO:10    5'-AACGTTGAGGGGCAT-3'
``` d) c-myb, for example

```
SEQ ID NO:11    5'-GTGCCGGGGTCTTCGGGC-3'
``` e) c-fos, for example

```
SEQ ID NO:12    5'-CGAGAACATCATCGTGG-3'
SEQ ID NO:13    5'-GGAGAACATCATGGTCGAAAG-3'
SEQ ID NO:14    5'-CCCGAGAACATCATGGTCGAAG-3'
SEQ ID NO:15    5'-GGGGAAAGCCCGGCAAGGGG-3'
``` f) p120, for example

```
SEQ ID NO:16    5'-CACCCGCCTTGGCCTCCCAC-3'
``` g) EGF receptor, for example

```
SEQ ID NO:17    5'-GGGACTCCGGCGCAGCGC-3'
SEQ ID NO:18    5'-GGCAAACTTTCTTTTCCTCC-3'
``` h) p53 tumor suppressor, for example

```
SEQ ID NO:19    5'-GGGAAGGAGGAGGATGAGG-3'
SEQ ID NO:20    5'-GGCAGTCATCCAGCTTCGGAG-3'
``` i) bcl-2, for example

```
SEQ ID NO:21    5'-TCTCCCAGCGTGCGCCAT-3'
``` j) VEGF, for example

```
SEQ ID NO:22    5'-GCGCTGATAGACATCCATG-3'
SEQ ID NO:23    5'-GGAGGCCCGACC-3'
SEQ ID NO:24    5'-GGTTTCGGAGGCC-3'
SEQ ID NO:25    5'-TGGTGGAGGTAG-3'
SEQ ID NO:26    5'-GCATGGTGGAGG-3'
SEQ ID NO:27    5'-TTGGCATGGTGG-3'
SEQ ID NO:28    5'-GCCTGGGACCAC-3'
SEQ ID NO:29    5'-CAGCCTGGGACC-3'
SEQ ID NO:30    5'-TGCAGCCTGGGA-3'
SEQ ID NO:31    5'-GTGCAGCCTGGG-3'
SEQ ID NO:32    5'-GGTGCAGCCTGG-3'
SEQ ID NO:33    5'-ATGGGTGCAGCC-3'
SEQ ID NO:34    5'-GGCTTGAAGATG-3'
SEQ ID NO:35    5'-GCAGCCCCCGCA-3'
SEQ ID NO:36    5'-GCAGCAGCCCCC-3'
``` k) c-raf kinase, for example

```
SEQ ID NO:37    5'-TCCCGCCTGTGACATGCATT-3'
``` l) PKC-alpha, for example

```
SEQ ID NO:38    5'-GTTCTCGCTGGTGAGTTTCA-3'
``` m) protein kinase A, for example

```
SEQ ID NO:39    5'-GCGTGCCTCCTCACTGGC-3'.
```

Pharmaceuticals comprising PNA derivatives of Formula I are furthermore suitable for treating diseases which are effected by integrins or cell-cell adhesion receptors, for example by VLA-4, VLA-2, ICAM, VCAM, or ELAM.

Antisense PNA derivatives which are active against such targets have, for example, the following base sequences:

a) VLA4, for example

SEQ ID NO:40    5'-GCAGTAAGCATCCATATC-3' b) ICAM-1, for example

SEQ ID NO:41    5'-GCCCAAGCTGGCATCCGTCA-3'
    SEQ ID NO:42    5'-CCCCCACCACTTCCCCTCTC-3'
    SEQ ID NO:43    5'-CTCCCCCACCACTTCCCCTC-3'
    SEQ ID NO:44    5'-GCTGGGAGCCATAGCGAGG-3' c) ELAM-1, for example

SEQ ID NO:45    5'-ACTGCTGCCTCTTGTCTCAGG-3'
    SEQ ID NO:46    5'-CAATCAATGACTTCAAGAGTTC-3' d) Integrin alpha(V), for example

SEQ ID NO:47    5'-GCGGCGGAAAAGCCATCG-3'.

Pharmaceuticals which comprise PNA derivatives of Formula I are also suitable for preventing restenosis. In this connection, it is possible to use PNA sequences which are directed against targets which are responsible for proliferation or migration. Examples of such targets are:
1) Nuclear transactivator proteins and cyclins, such as, for example, c-myc, c-myb, c-fos, c-fos/jun, cyclins, and cdc2 kinase;
2) Mitogens or growth factors, such as, for example, PDGF, bFGF, VEGF, EGF, HB-EGF, and TGF-β; and
3) Cell receptors, such as, for example, bFGF receptor, EGF receptor, and PDGF receptor.

Antisense PNA derivatives which are active against such targets have, for example, the following base sequences:
a) c-myb, for example

SEQ ID NO:48    5'-GTGTCGGGGTCTCCGGGC-3' b) c-myc, for example

SEQ ID NO:49    5'-CACGTTGAGGGGCAT-3' c) cdc2 kinase, for example

SEQ ID NO:50    5'-GTCTTCCATAGTTACTCA-3' d) PCNA (proliferating cell nuclear antigen of rat), for example

SEQ ID NO:51    5'-GATCAGGCGTGCCTCAAA-3'.

PNA derivatives can likewise be used for treating vitiligo and other depigmentation diseases or depigmentation disturbances (e.g. of the skin, the hair, and the eyes), such as albinism and psoriasis. They can also be used for treating asthma. In embodiments, expression of the adenosine A1 receptor, the adenosine A3 receptor, the bradykinin receptor, or IL-13 is inhibited using suitable antisense agents. An example of a base sequence for such applications is:

SEQ ID NO:52    5'-GATGGAGGGCGGCATGGCGGG-3'.

Pharmaceuticals that comprise a PNA derivative of Formula I can be used, for example, in the form of pharmaceutical preparations which can be administered orally, for example in the form of tablets, coated tablets, hard or soft gelatin capsules, solutions, emulsions, or suspensions. They can also be administered rectally, e.g. in the form of suppositories, or parenterally, e.g. in the form of solutions for injection. In order to produce pharmaceutical preparations, these compounds can be processed in therapeutically inert organic and inorganic excipients. Non-limiting examples of such excipients for tablets, coated tablets, and hard gelatin capsules are lactose, cornstarch or derivatives thereof, tallow, and stearic acid or salts thereof. Suitable excipients for preparing solutions include, but are not limited to, water, polyols, sucrose, invert sugar, and glucose. Suitable excipients for injection solutions include, but are not limited to, water, alcohols, polyols, glycerol, and vegetable oils. Suitable excipients for suppositories include, but are not limited to, vegetable oils and hydrogenated oils, waxes, fats, and semiliquid polyols. The pharmaceutical preparations can also comprise preservatives, solvents, stabilizers, wetting agents, emulsifiers, sweeteners, dyes, flavorants, salts (e.g., for altering the osmotic pressure), buffers, coating agents, antioxidants and, where appropriate, other therapeutically active compounds. The identity and amount of excipient, carrier, and/or additive should conform to the practices known to those of skill in the pharmaceutical art. Techniques for preparation of pharmaceuticals according to the present invention are well known to those of skill in the art and are well within the skill of those artisans. Accordingly, the techniques need not be detailed here. Treatment regimens (e.g., number of doses per unit time, length of treatment, etc.) should conform to the practices known to those of skill in the pharmaceutical art.

Administration forms include, but are not limited to, topical applications; local applications, for example using a catheter or by inhalation; injections; infusions; and oral administration. For injection, the PNA derivatives of Formula I are formulated in a liquid solution, such as a physiologically acceptable buffer (for example Hank's solution or Ringer's solution). However, the oligonucleotides can also be formulated in solid form and dissolved or suspended before use. Suitable doses for systemic administration are from about 0.01 mg/kg to about 50 mg/kg of bodyweight and per day.

Thus, the invention furthermore relates to pharmaceutical preparations which comprise PNA derivatives of Formula I and/or their physiologically tolerated salts in addition to pharmaceutically acceptable excipients and/or additives.

The PNA derivatives of Formula I and/or their physiologically tolerated salts can be administered to animals, including mammals. In embodiments, the mammal is a human. In embodiments, the mammal is a feline, such as a cat or a canine, such as a dog. In embodiments, the mammal is an equine, such as a horse; an ovine, such as a cow or steer; a porcine, such as a pig; or an ovine, such as a sheep.

In embodiments, the PNA derivatives and/or their physiologically tolerated salts are administered in the form of pharmaceuticals. In embodiments, they are administered without additional components (such as those that are included in pharmaceuticals). In embodiments, they are administered in mixtures with each other. In embodiments, they are administered in the form of pharmaceutical preparations which permit topical, percutaneous, parenteral, or enteral use and which comprise, as the active constituent, an effective dose of at least one PNA derivative together with customary, pharmaceutically acceptable (i.e., tolerable) excipients and/or additives. The preparations can comprise from about 0.1 to 90% by weight of the therapeutically active compound. A topical application, for example in the form of ointments, lotions, tinctures, emulsions, or suspensions, is suitable for treating skin diseases.

As discussed above, the pharmaceutical preparations are produced in a manner known to those of skill in the art (see, for example, Remington's Pharmaceutical Sciences, Mack Publ. Co., Easton, Pa.), with pharmaceutically inert inorganic and/or organic excipients being used where appropriate. It is possible, for example, to use lactose, cornstarch and/or derivatives thereof, tallow, stearic acid and/or its salts, etc., for producing pills, tablets, coated tablets and hard gelatin capsules. Non-exclusive examples of excipients for soft gelatin capsules and/or suppositories are fats, waxes, semisolid and liquid polyols, natural and/or hydrogenated oils, etc. Suitable excipients for producing solutions and/or syrups are, for example, water, sucrose, invert sugar, glucose, polyols, etc. Suitable excipients for producing solutions for injection are, for example, water, alcohols, glycerol, polyols, vegetable oils, etc. Suitable excipients for microcapsules, implants, and/or rods include, but are not limited to, copolymers consisting of glycolic acid and lactic acid. Liposome formulations which are known to the skilled person (see, for example, N. Weiner, Drug Develop Ind Pharm 15 (1989) 1523; "Liposome Dermatics, Springer Verlag 1992), for example HVJ liposomes (Hayashi, Gene Therapy 3 (1996) 878) are also suitable. Dermal application can also be effected, for example, using ionophoretic methods and/or using electroporation.

In addition to the active compounds and excipients, a pharmaceutical preparation can also contain additives, such as fillers, extenders, disintegrants, binders, glidants, wetting agents, stabilizers, emulsifiers, preservatives, sweeteners, dyes, flavorants or aromatizing agents, thickeners, diluents, and buffering substances. It can also contain solvents and/or solubilizing agents and/or agents for achieving a sustained release effect, and also salts, for example, for altering the osmotic pressure, coating agents, and/or antioxidants. A pharmaceutical preparation can also comprise two or more different PNA derivatives of Formula I and/or their physiologically tolerated salts and also, furthermore, in addition to at least one PNA derivative of Formula I, one or more different therapeutically active substances. The dose can vary within wide limits and is to be adjusted to the individual circumstances in each individual case. As mentioned above, regulating dosage is well within the abilities of those of skill in the art.

The invention furthermore relates to the use of PNA derivatives of Formula I as diagnostic agents, for example, as aids in DNA diagnosis and in molecular biology (see, for example: Peptide Nucleic Acids: Protocols and Applications; Peter E. Nielsen and Michael Egholm (Edit.) Horizon Scientific Press, 1999). In DNA diagnosis, gene probes, also termed DNA probes or hybridization probes, play an important role in the sequence-specific detection of particular genes. In general, a gene probe consists of a recognition sequence and one or more suitable labeling groups (labels). The specificity with which a target sequence in an analytical sample is identified by means of hybridization with a complementary gene probe is determined by the recognition sequence and its chemical structure. This technique can also be applied to PNA. As compared with oligonucleotides having a natural structure, PNA has the advantage that it has a higher affinity for the target sequence and a greater ability to discriminate between bases.

In an embodiment, the PNA are used in a method for detecting a nucleic acid of interest. In the method, the PNA is labeled with a detectable label, wherein the PNA derivative comprises a base sequence that specifically hybridizes with at least one sequence present in the nucleic acid of interest under selected conditions (for example, stringency conditions that permit specific hybridization). The labeled PNA is combined with a sample suspected of containing the nucleic acid of interest under conditions where specific binding of the PNA derivative to the nucleic acids in the sample can occur. Specific binding of the PNA derivative and nucleic acids present in the sample can then be detected using techniques suitable for the label and known to those of skill in the art. Specific binding indicates the presence of the nucleic acid of interest in the sample.

In embodiments, the nucleic acid is a viral nucleic acid. In embodiments, the nucleic acid is a nucleic acid from a microorganism (e.g., bacterium).

The use of the compounds of Formula I therefore also relates to in-situ hybridization and fluorescence in-situ hybridization (FISH). In-situ hybridization can also be used, for example, for detecting microorganisms and viruses (Just et al. (1998) J. Vir. Method. 73, 163-174).

Another application of the compounds of the invention relates to detecting and quantifying nucleic acids. Methods for performing such assays can follow along the steps provided above, with the additional step of quantifying the detected nucleic acid using techniques known to those of skill in the art, for example, comparison to concentration standard curves, extrapolation based on extinction coefficients, etc. In addition, for quantitation, use can be made of array technology (Strother et al. J. Am. Chem. Soc. (2000) 122, 1205-1209; Niemeyer et al., Angew. Chem. (1999) 111, 3039-3043; Pirrung (1997) Chem. Rev. 97, 473-488), which provides high sample throughput and a high degree of sensitivity. In this case, the PNA probes are fixed on a suitable support or PNA chip. To achieve this, PNA can be synthesized as described in the examples and subsequently fixed onto the support or PNA chip. Alternatively, the PNA can be prepared directly on the support. Another application is the use of the compounds of Formula I as biosensors for detecting nucleic acids (Wang et al (1996) J. Am. Chem. Soc. 118, 7667). In such a method, the PNA derivative is associated with a sensor such that interaction of the PNA with a target molecule produces a signal that is transmitted through the sensor and to a detection device, which then indicates whether interaction has occurred. The use of PNA of Formula I possessing an affinity label, such as histidyl-PNA, is another application for purifying nucleic acids (Oerum et al. (1999), in Peptide Nucleic Acids: Protocols and Applications).

The PNA backbone can be synthesized using the methods described in the literature, for example using the tert-butyloxycarbonyl (BOC), 9-fluorenylmethoxycarbonyl (Fmoc), or monomethoxytrityl (Mmt) protecting group strategy (Peptide Nucleic Acids: Protocols and Applications; Peter E. Nielsen and Michael Egholm (Edit.) Horizon Scientific Press, 1999). In embodiments, the Mmt protecting group is used for temporarily protecting the amino function of the aminoethylglycine and base-labile protecting groups on the heterocyclic nucleobases (D. Will et al. (1995) Tetrahedron 51, 12069; Breipohl et al. (1997) Tetrahedron 53, 14671-14686). Examples of monomeric building blocks are compounds of Formulae V to VB (below), with A, B, D, E, u', and U having the meanings defined above. PG can be an amino-protecting group such as benzoyl, anisoyl-, isobutyroyl-, acetyl-, or tert-butylbenzoyl (Breipohl et al. (1997) Tertrahedron 53, 14671-14686). TR can be an acid-labile protecting group such as dimethoxytrityl (Dmt) (for U=O and S) or Mmt (for U=NH).

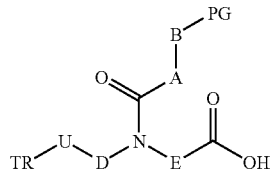

Formula V

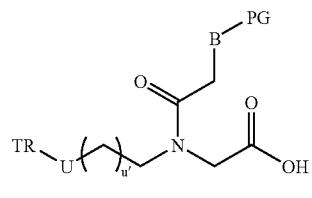

Formula V A

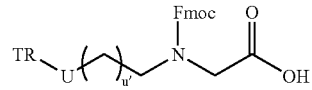

Formula V B

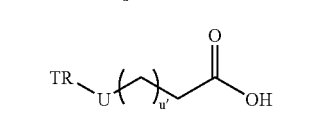

Formula V C

After the PNA backbone has been constructed, the free amino function of the N terminus can be reacted directly with an appropriate phosphorylating reagent, for example to yield the corresponding phosphoramidate (U=NR$_1$ in Formula I)

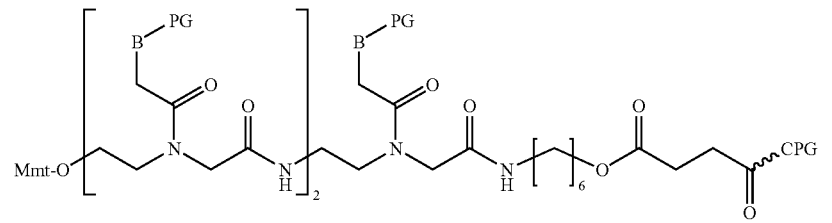

1. 3% TCA in DCM
2. Tetrazole + 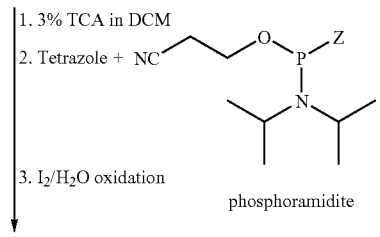
   phosphoramidite
3. I$_2$/H$_2$O oxidation

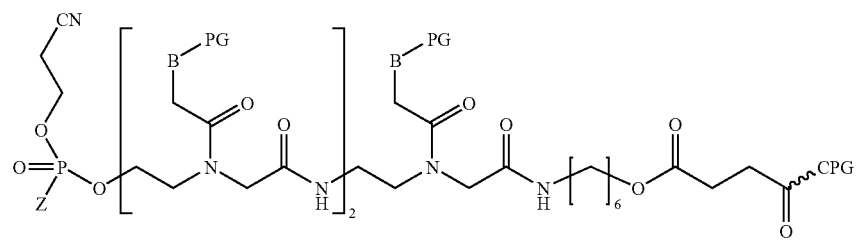

NH$_4$OH

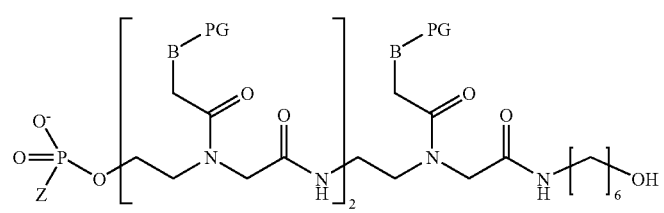

Figure 4A:
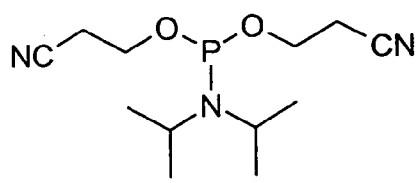
FIGS. 4a, 4b, 4c and 4d show examples of phphohorylating reagents.
Figure 4A:
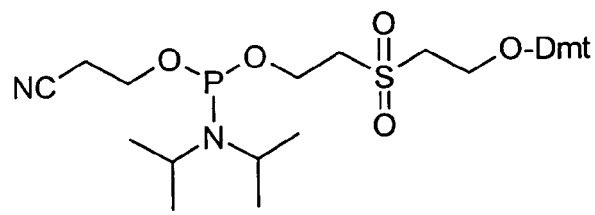
Figure 4A:
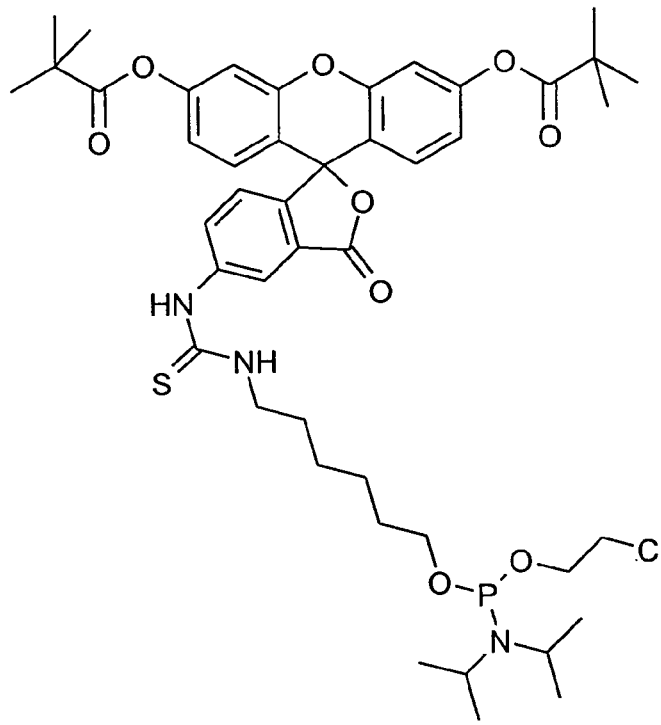
Figure 4B:
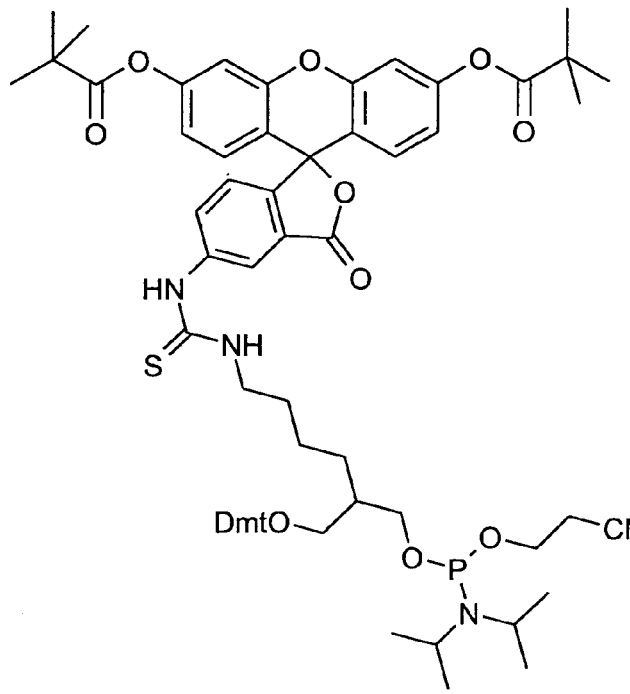
Figure 4B:
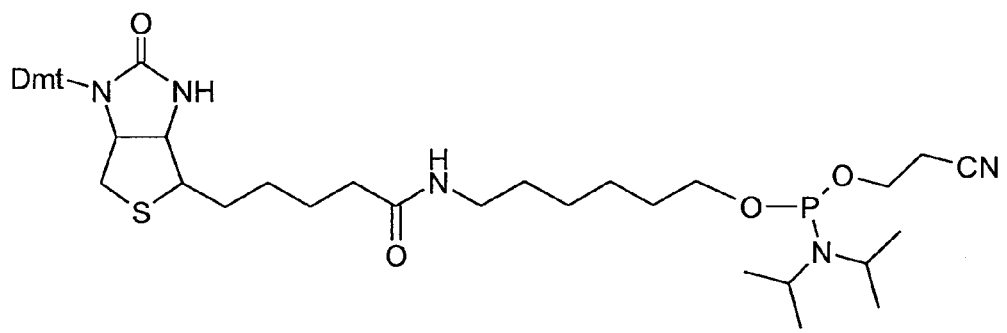
Figure 4B:
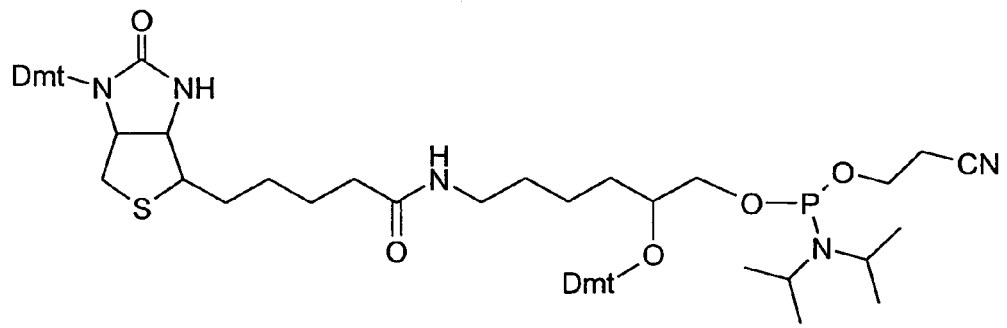

In this way, PNA-7 in Example 8 (U=NH) can be obtained, for example, by reacting the N terminus (at the building block which was coupled on last, wherein B=adenine) with biotin-phosphoramidite 5 (FIG. 4b). Alternatively, a Dmt-protected hydroxyalkyl building block (for U=O) or a Dmt-protected mercaptoalkyl building block (for U=S) of the Formula V A can be coupled on in the last cycle. After the Dmt group has been eliminated, the free hydroxy or mercapto function can be reacted, for example, with phosphorylation reagent 1 (FIG. 4a). Following oxidation, cleavage from the support and removal of the protecting groups, the phosphate (V=W=X=Y=O) or thiophosphate (V=S, W=X=Y=O) of Formula I is obtained. If the amino terminal unit does not contain any nucleobase (i.e., B is hydrogen), the building block shown in Formula VB is used in the condensation reaction of the last cycle, with the Fmoc protecting group being eliminated with ammonia at the end of the synthesis. The amino terminus of the PNA can be extended by condensing building blocks of the Formula VC before the actual phosphorylation reaction is carried out.

The phosphoryl radicals can be introduced using the reagents which are customarily employed in nucleotide chemistry, for example by means of the phosphoramidite method, the H-phosphonate method, or the phosphotriester method (E. Sonveaux (1986) Bioorganic Chemistry 14, 274; S. L. Beaucage and R. P. Iyer (1993) Tetrahedron 49, 1925; E. Uhlmann and A. Peyman (1990) Chem. Rev. 90, 543). There are a large number of phosphorylating reagents available (see, for example, Glen Research Corporation, Sterling, Va. 20164, USA) which can be used for preparing the compounds of Formula I. A selection of the reagents is shown in FIGS. 4a to 4d, with the invention not, however, being restricted to these special derivatives. In the above-described phosphorylation reaction, Z can also have the meaning of X, with reactive functions being protected in intermediate steps with suitable protecting groups.

The phethora of amino terminal modification can be illustrated on the basis of the synthesis of PNA-6, PNA-12, PNA-13, and PNA-14. First of all, the PNA t(oeg)-at tcc gtc at-hex-CPG (PNA bases are abbreviated with small letters for the corresponding nucleobases; oeg stands for hydroxyethylglycine) is synthesized, in fully protected form, on the CPG (controlled pore glass) support, which carries a hydroxyethylglycine-(oeg)-acetylthymine as the last building block. The hydroxyl group can now be reacted individually with phosphoramidites 1, 5, 7, and 3, respectively. Following oxidation, elimination of the protecting groups and cleavage of the product from the CPG support, PNA-6, PNA-12, PNA-13, and PNA-14, respectively, are correspondingly obtained. TENTAGEL® (from Rapp Polymers GmbH, Tübingen) and aminomethylpolystyrene are also used as solid supports.

In principle, all the reagents which are known in nucleotide chemistry are suitable for introducing the phosphoryl function. For example, the following reagents of Formulae VIA, VIB, VIC, and VID can be used:

Formula VI A

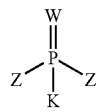
Formula VI B

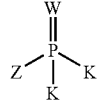
Formula VI C

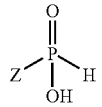
Formula VI D wherein K is halogen (for example Cl), triazolyl, imidazolyl, or dialkylamino, and Z has the above-mentioned meaning or the meaning of X, with reactive groups being appropriately protected. For example, the hydroxyl groups of the fluorescein-phosphoramidite 3 (FIG. 4a) can be protected by esterifying with pivalic acid.

The compounds of Formula VI are only to be regarded as being examples of such reagents, which react, where appropriate, in the added presence of other auxiliary reagents such as bases, acids, or condensing reagents. In embodiments, reagents of Formula VI A, which react in accordance with the phosphoramidite method (Beaucage and Iyer, 1993) are used. These reagents are reacted as the phosphorus (III) compound and subsequently oxidized to phosphorous (V). If, for example, the oxidation is carried out using iodine/water/pyridine or tert-butyl hydroperoxide, the phosphoryl derivatives (W=O) are then obtained. If, on the other hand, the oxidation is carried out using elemental sulfur or Beaucage reagent, the corresponding thiophosphoryl compound (W=S) is then obtained.

Among the reagents (FIGS. 4a to 4d) are also to be found "bifunctional reagents" which, because of the possession of a second function, which is initially protected, can be caused to react several times. The phosphoramidites 4, 6, and 8 to 13 are examples of such bifunctional reagents. In this connection, it can be a matter of the multiple conjugation of a reagent or else of successive reaction with different reagents. Thus, for example, the fluorescein-phosphoramidite 3 can only be caused to react once. By comparison, the fluorescein-phosphoramidite 4 possesses a Dmt group-protected hydroxyl function which can be reacted once again with a phosphorylating reagent after the Dmt group has been eliminated. In this way, it is possible to introduce one and the same group or different groups several times. PNA-16 is an example of a multiple conjugation. After the PNA chain had been synthesized, a hydroxyethyleneglycine-C building block was coupled on in the last cycle, with this building block being reacted successively twice with the spacer 18 phosphoramidite 9, the amino-modifier 5 phosphoramidite 12, and finally with lexitropsin of Formula VII while activating with peptide coupling reagents such as HBTU. The coupling of an amino-modifier permits the subsequent introduction of a further residue, which can be introduced in the form of an activated carboxylic acid derivative. In this connection, it is also possible, for example, to use isothiocyanates and N-hydroxysuccinimide esters.

Formula VII

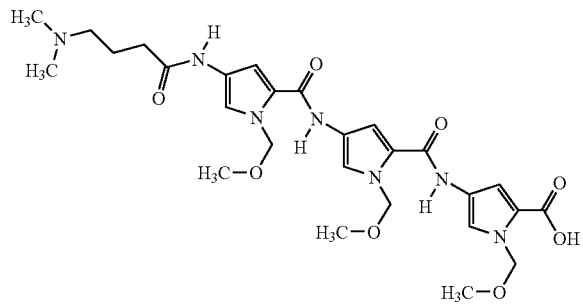

Figure 5A:
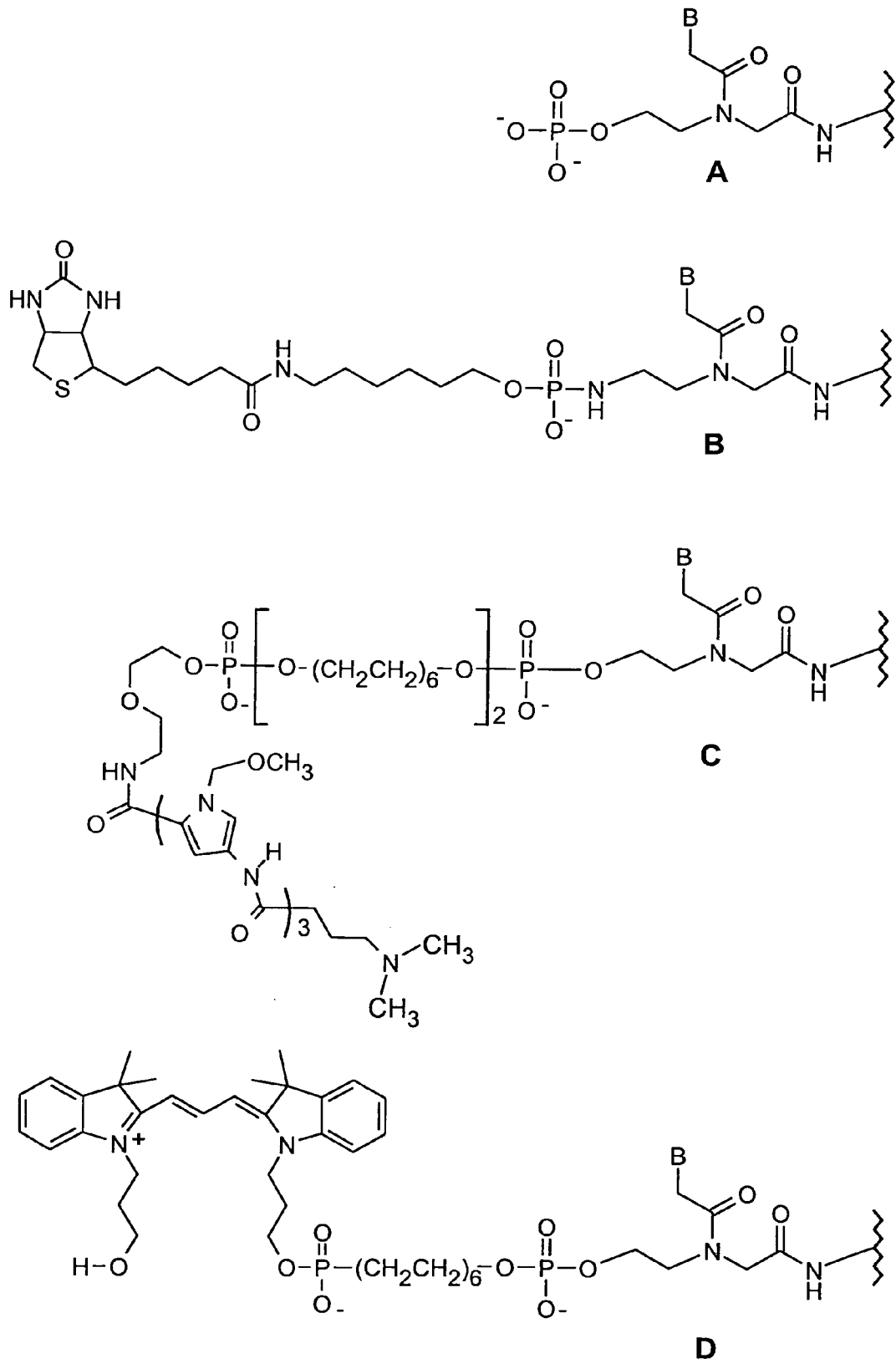
FIGS. 5a and 5b show examples of single (A, B) and multiple (C to F) N-terminal derivatization of PNA.
Figure 5B:
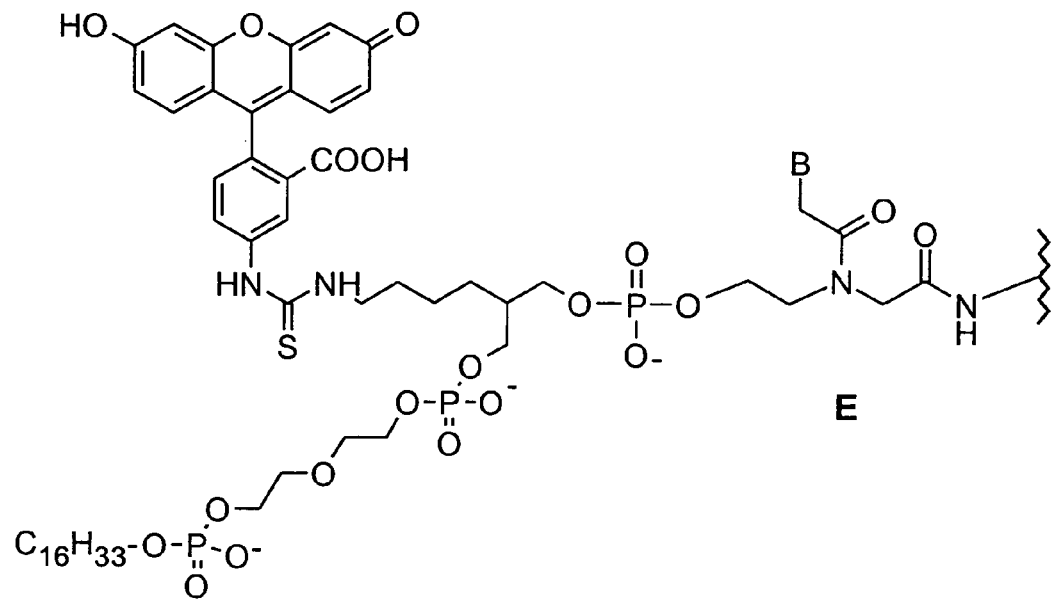
Figure 5B:
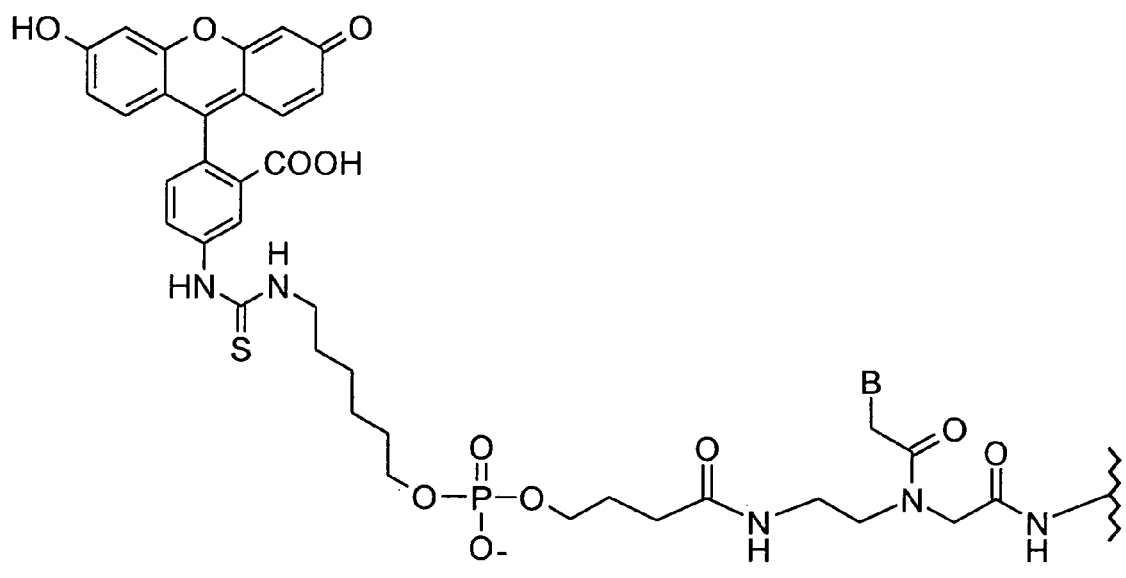

FIGS. 5a and 5b show some examples of compound types for the N-terminal modification of the compounds of Formula I. Compound type A is obtained by reacting the terminal hydroxyl group of the PNA with the phosphorylation reagent 1. Compound type B is obtained by reacting the terminal amino group of the PNA with the biotin-phosphoramidite 5. Compound type C is obtained by successively reacting the PNA having a terminal hydroxyl group with the spacer-18 phosphoramidite 9, amino modifier-5 phosphoramidite 12, and lexitropsin. Compound type D is obtained by successively reacting the PNA having a terminal hydroxyl group with the spacer-9 phosphoramidite 8 and the cyanine-3 phosphoramidite 10. Compound type E is obtained by successively reacting the PNA having a terminal hydroxyl group with the bifunctional fluorescein-phosphoramidite 4, the spacer-9 phosphoramidite 8, and the $C_{16}$-phosphorylating reagent 7. Compound type F is obtained by reacting the terminal amino group of the PNA with 4-hydroxybutyric acid, whose hydroxyl function is temporarily protected with a Dmt group, and subsequently reacting with the fluorescein-phosphoramidite 3. The steps which additionally have to be carried out, such as oxidation and protecting group elimination are described in the examples.

In embodiments, the process for preparing a PNA derivative of the invention comprises: a) synthesizing a backbone for the PNA derivative, starting from the C terminus, by sequentially coupling with amidonucleic acid monomers, which are optionally N-terminally protected; b) optionally deprotecting the N-terminally protected PNA backbone; c) coupling a phosphorus (III) or a phosphorus (V) group to the N-terminus of the PNA backbone, using activatied phosphorylating reagents optionally containing a spacer, d) optionally repeating step c); and e) optionally oxidizing the phosphorus (III) group to a phosphorus (V) group.

EXAMPLES

The following examples are presented to more fully describe selected embodiments of the invention. The following examples are not intended, and should not be construed, to limit the invention in any way.

The preparation of the following compounds is described by way of example:

PNA-1 to PNA-6:

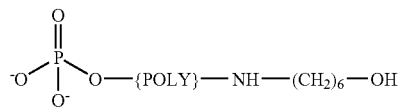

PNA-7:

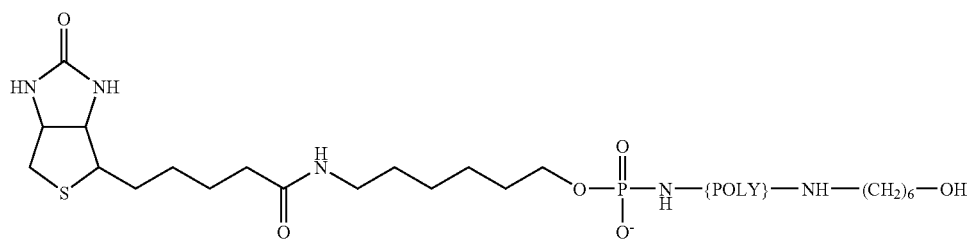

PNA-8 to PNA-12:

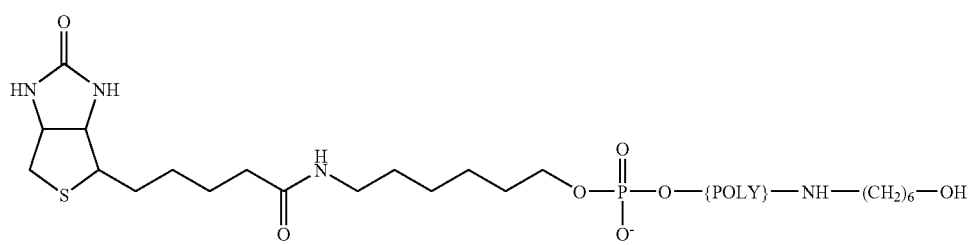

-continued
PNA-13:
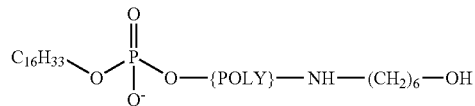
PNA-14:
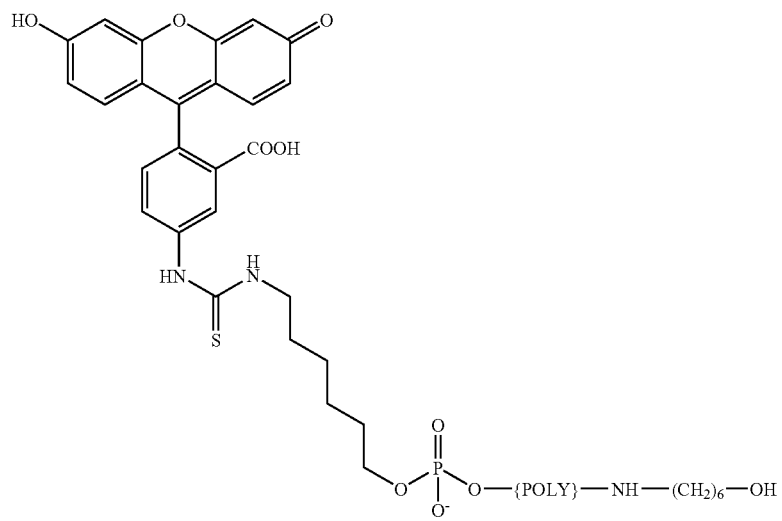
PNA-15:
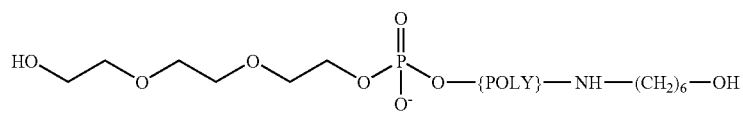
PNA-16:
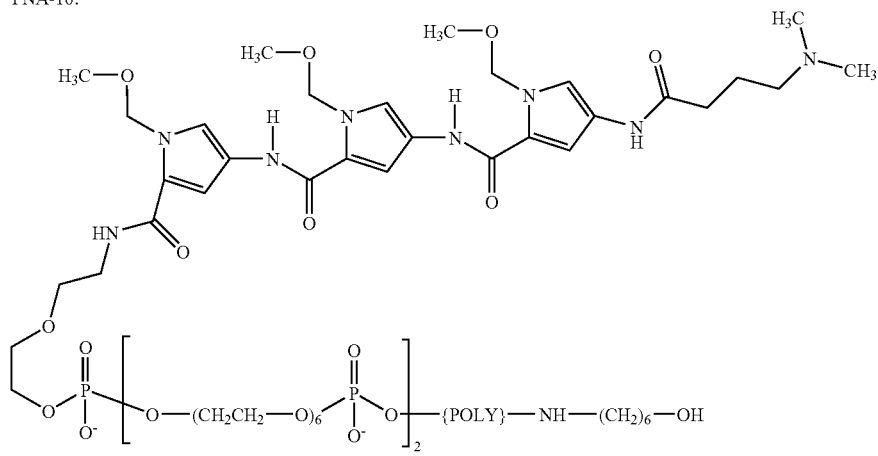
PNA-17:
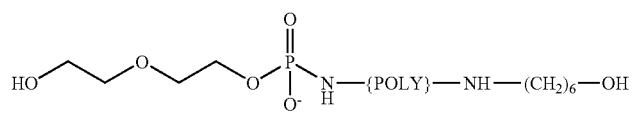
PNA-18:
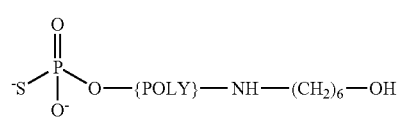

wherein the base sequences in each case are described by the following sequences,

| SEQ ID NO:53 | 5'-AACT-3' | (PNA-1) |
| SEQ ID NO:54 | 5'-ACATCATGGTCG-3' | (PNA-2) |
| SEQ ID NO:55 | 5'-CCACGATGATGT-3' | (PNA-3) |
| SEQ ID NO:56 | 5'-GAGCCATGTATAGTGAC-3' | (PNA-4) |
| SEQ ID NO:57 | 5'-TCGGTTTGAGATCTGG-3' | (PNA-5) |
| SEQ ID NO:58 | 5'-TATTCCGTCAT-3' | (PNA-6, PNA-12, PNA-13, PNA-14, PNA-18) |
| SEQ ID NO:59 | 5'-ACTGATGTAGTC-3' | (PNA-7) |
| SEQ ID NO:60 | 5'-GCTGATGTAGTC-3' | (PNA-8) |
| SEQ ID NO:61 | 5'-GGTATGGGATAT-3' | (PNA-9, PNA-11) |
| SEQ ID NO:62 | 5'-TGAAGGAAGAGG-3' | (PNA-10) |
| SEQ ID NO:63 | 5'-GTTAGGGTTAG-3' | (PNA-15, PNA-17) |
| SEQ ID NO:64 | 5'-CCCCTTCC-3' | (PNA-16) | and wherein {POLY} is described by Formula II and {BLOCK} is in each case described by Formula IIIA, and where, in addition, A and E are $CH_2$ and D is $(CH_2)_2$, and z' in each case ensues from the length of the sequence of the oligomer.

Example 1

Synthesizing the PNA Chain

The following reagents were used for preparing the PNA moiety:
1. Phosphoramidite reagent (0.1 M in acetonitrile (ACN))
2. Mmt-PNA monomers and/or Dmt-oeg-PNA monomers (0.2 M in DMF:ACN (1:1; v:v))
3. Anhydrous ACN (≦30 ppm of water)
4. Trichloroacetic acid (3%) in dichloromethane (DCM)
5. Acetic anhydride, 2,6-lutidine in THF (1:1:8; v:v:v); (Cap A)
6. N-Methylimidazole (16%) in THF; (Cap B)
7. Iodine solution (0.05 M) in THF, water, pyridine (7:2:1; v:v:v)
8. Washing solution (THF, water, pyridine (7:2:1; v:v:v))
9. Tetrazole (0.3 M) in ACN
10. HBTU; 0.2 M in DMF:ACN (1:1; v:v)
11. DIPEA; 0.2 M in DMF:ACN (1:1; v:v)
12. DMF (>99.5%)
13. Solid phase support: aminopropyl-CPG (550 Å) loaded with Mmt-aminohex-1-yl hemisuccinate (for PNA-hexylamides).

The Mmt/acyl-protected or Dmt/acyl-protected oeg monomers were prepared as has already been described (Breipohl et al. (1997) Tetrahedron 53, 14671-14686). The loading of aminopropyl-CPG with the Mmt-aminohex-1-yl hemisuccinate has already been described as well (Will et al. (1995) Tetrahedron 51, 12069-12082). The PNA syntheses were in general carried out on a scale of from 2 to 5 µmol.

The following cycle was used for the PNA synthesis:
1. Step of washing with ACN
2. Deprotecting the Mmt group or the Dmt group by treating with 3% trichloroacetic acid (TCA) in DCM; 110 sec.
3. Step of washing with DMF/ACN (1:1)
4. Neutralizing with DIPEA in DMF/ACN (1:1)
5. Coupling on the monomeric building block by preactivating (15 min) with HBTU/DIPEA/PNA monomer (ratio 1:1:1; total volume 450 µl) charging the solid phase and coupling (45 min)
6. Step of washing with ACN
7. Capping with acetic anhydride/N-methylimidazole
8. Step of washing with ACN
9. New cycle Example 2

Synthesizing Phosphate-{a(oeg)act}-hex (PNA-1)

The PNA moiety was prepared by solid phase synthesis as described in Example 1 (2 µmol synthesis). In the last cycle, a hydroxyethylglycine (oeg)-based building block having an adenine as the nucleobase was coupled on (Formula V A; wherein TR is Dmt, U is oxygen, u' is 2, PG is anisoyl and B is adenine). After the terminal Dmt group was eliminated with 3% TCA, the free hydroxyl function was reacted with phosphorylating reagent 1 (FIG. 4a) using tetrazole as catalyst. This reaction employs an excess of the phosphorylating reagent 1 (approx. 25-fold), as a 0.3 M solution in acetonitrile/tetrahydrofuran (1:1; v:v) and the tetrazole (approx. 50-fold; 0.5 M in acetonitrile). After the condensation had taken place, oxidation was effected using an iodine solution (0.05 M in tetrahydrofuran/water, pyridine (7:2:1; v:v:v)). The PNA was then cleaved from the support, and the protecting groups removed at the same time, by treating with concentrated ammonia at 50° C. overnight. 83 OD (260 nm) was obtained. Of these, 40 OD was purified by preparative polyacrylamide (PAA) gel electrophoresis. The band of desired product was eluted with 0.2 M triethylammonium bicarbonate buffer and desalted through a Bond-Elut C18 column (1 g). 13.5 OD was obtained. The product was analyzed by negative ion mass spectrometry, which confirmed the calculated mass (calc. 1266.2; found 1265.9).

Example 3

Synthesizing Phosphate-{a(oeg) ca tca tgg tcg}-hex (PNA-2)

The preparation was effected, in a 2 µmol synthesis, in an analogous manner to that described in Example 2. Following cleavage with ammonia, 122 OD of crude product was obtained, with this crude product being purified by electrophoresis through a 15% PAA gel. 27 OD was obtained. The product was analyzed by negative ion mass spectrometry, which confirmed the calculated mass (calc. 3450.3; found 3450.4).

Example 4

Synthesizing Phosphate-{c(oeg) ca cga tga tgt}-hex (PNA-3)

The preparation was effected, in a 2 µmol synthesis, in an analogous manner to that described in Example 2, with a hydroxyethylglycine-based building block having cytosine as the nucleobase being coupled on in the last cycle.

Following cleavage with ammonia, 124 OD of crude product was obtained, with this crude product being purified by electrophoresis through a 15% PAA gel. 19 OD was obtained. The product was analyzed by negative ion mass spectrometry, which confirmed the calculated mass (calc. 3450.3; found 3450.1).

Example 5

Synthesizing Phosphate-{g(oeg)-ag cca tgt ata gtg ac}-hex (PNA-4)

The preparation was effected, in a 2 μmol synthesis, in an analogous manner to that described in Example 2, with a hydroxyethylglycine-based building block having guanine as the nucleobase being coupled on in the last cycle. Following cleavage with ammonia, 120 OD of crude product was obtained. 60 OD of the crude product was purified by electrophoresis through a 15% PAA gel. 10 OD was obtained. The product was analyzed by negative ion mass spectrometry, which confirmed the calculated mass (calc. 4848.6; found 4849.9).

Example 6

Synthesizing Phosphate-{t(oeg)cg gtt tga gat ctg g}-hex (PNA-5)

The preparation was effected, in a 2 μmol synthesis, in an analogous manner to that described in Example 2, with a hydroxyethylglycine-based building block having thymine as the nucleobase being coupled on in the last cycle. Following cleavage with ammonia, 250 OD of crude product was obtained. 60 OD of the crude product was purified by eletrophoresis through a 15% PAA gel. 22.9 OD was obtained. The product was analyzed by negative ion mass spectrometry, which confirmed the calculated mass (calc. 4595.4; found 4596.3).

Example 7

Synthesizing Phosphate-{t(oeg)-at tcc gtc at}-hex (PNA-6)

The preparation was effected in a 0.5 μmol synthesis, in an analogous manner to that described in Example 2, with a hydroxyethylglycine-based building block having thymine as the nucleobase being coupled on in the last cycle. Following cleavage with ammonia, 63 OD of crude product was obtained. 30 OD of the crude product was purified by electrophoresis through a 15% PAA gel. 4.2 OD was obtained. The product was analyzed by negative ion mass spectrometry, which confirmed the calculated mass (calc. 3124.5; found 3124.8).

Example 8

Synthesizing Biotin-p-{act gat gta gtc}-hex (PNA-7)

The PNA moiety was prepared by solid phase synthesis as described in Example 1 (2 μmol synthesis). In the last cycle, a normal PNA building block, having adenine as the nucleobase, was coupled on (Formula VA; wherein TR is Mmt, U is NH, u' is 2, PG is anisoyl, and B is adenine). After eliminating the terminal Mmt group with 3% TCA, the free amino function was reacted with biotin-phosphoramidite 5 (FIG. 4b) using tetrazole as catalyst. This reaction employs an excess of the phosphorylating reagent (approx. 10-fold) as a 0.12 M solution in acetonitrile and the tetrazole (approx. 5-fold; 0.5 M in acetonitrile). After the condensation had taken place, oxidation was effected using an iodine solution (0.05 M in tetrahydrofuran/water, pyridine (7:2:1; v:v:v)). After cleaving with ammonia, 288 OD of crude product was obtained. The crude product was purified by electrophoresis through a 15% PAA gel. 17.5 OD was obtained. The product was analyzed by negative ion mass spectrometry, which confirmed the calculated mass (calc. 3789.6; found 3789.8).

Example 9

Synthesizing Biotin-p-{g(oeg)-ct gat gta gtc}-hex (PNA-8)

The PNA moiety was prepared by solid phase synthesis as described in Example 1 (1 μmol synthesis). A hydroxyethyleneglycine-based building block having guanine as the nucleobase (Formula VA; wherein TR is Dmt, U is oxygen, u' is 2, PG is anisoyl and B is guanine) was coupled on in the last cycle. After eliminating the terminal Dmt group with 3% TCA, the free hydroxyl function was reacted with biotin-phosphoramidite 5 (FIG. 4b) using tetrazole as catalyst. This reaction employs an excess of the phosphorylating reagent (approx. 10-fold) as a 0.12 M solution in acetonitrile and the tetrazole (approx. 50-fold; 0.5 M in acetonitrile). After the condensation had taken place, oxidation was effected using an iodine solution (0.05 M in tetrahydrofuran/water, pyridine (7:2:1; v:v:v)). After cleaving with ammonia, 63 OD of crude product was obtained. The crude product was purified by electrophoresis through a 15% PAA gel. 11.2 OD was obtained. The product was analyzed by negative ion mass spectrometry, which confirmed the calculated mass (calc. 3806.8; found 3807.2).

Example 10

Synthesizing Biotin-p-{g(oeg) gt atg gga tat}-hex (PNA-9)

The preparation was effected, in a 2 μmol synthesis, in an analogous manner to that described in Example 9, with a hydroxyethylglycine-based building block having guanine as the nucleobase being coupled on in the last cycle. The biotin residue was introduced with biotin-phosphoramidite 5 (FIG. 4b). After cleaving with ammonia, 274 OD of crude product was obtained. The crude product was purified by electrophoresis through a 15% PAA gel. 25.8 OD was obtained. The product was analyzed by negative ion mass spectrometry, which confirmed the calculated mass (calc. 3870.8; found 3869.7).

Example 11

Synthesizing Biotin-p-{t(oeg) ga agg aag agg}-hex (PNA-10)

The preparation was effected, in a 2 μmol synthesis, in an analogous manner to that described in Example 9, with a hydroxyethylglycine-based building block having thymine as the nucleobase being coupled on in the last cycle. The biotin residue was introduced with biotin-phosphoramidite 5 (FIG. 4b). After cleaving with ammonia, 190 OD of crude product was obtained. The crude product was purified by electrophoresis through a 12% PAA gel. 29 OD was obtained with the expected molecularweight (calc. 3913.9; found 3913.7).

Example 12

Synthesizing Biotin-p-{g(oeg)-gt atg gga tat}-hex (PNA-11)

The preparation was effected, in a 2 µmol synthesis, in an analogous manner to that described in Example 9, with a hydroxyethylglycine-based building block having guanine as the nucleobase being coupled on in the last cycle. The biotin residue was introduced with biotin-phosphoramidite 5 (FIG. 4b). After cleaving with ammonia, 162 OD of crude product was obtained. The crude product was purified by electrophoresis through a 12% PAA gel. 21 OD was obtained. The product was analyzed by negative ion mass spectrometry, which confirmed the calculated mass (calc. 3870.8; found 3870.8).

Example 13

Synthesizing Biotin-p-{t(oeg) at tcc gtc at}-hex (PNA-12)

The preparation was effected, in a 0.5 µmol synthesis, in an analogous manner to that described in Example 9, with a hydroxyethylglycine-based building block having thymine as the nucleobase being coupled on in the last cycle. The biotin residue was introduced with biotin-phosphoramidite 5 (FIG. 4b). After cleaving with ammonia, 67 OD of crude product was obtained. The crude product was purified by electrophoresis through a 12% PAA gel. 8.5 OD was obtained. The product was analyzed by negative ion mass spectrometry, which confirmed the calculated mass (calc. 3449.5; found 3449.9).

Example 14

Synthesizing Hexadecyl-O-p-{t(oeg) at tcc gtc at}-hex (PNA-13)

Figure 4C:
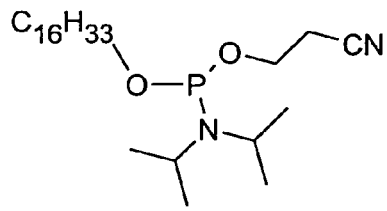
Figure 4C:
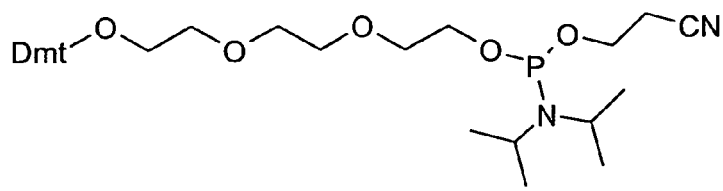
Figure 4C:
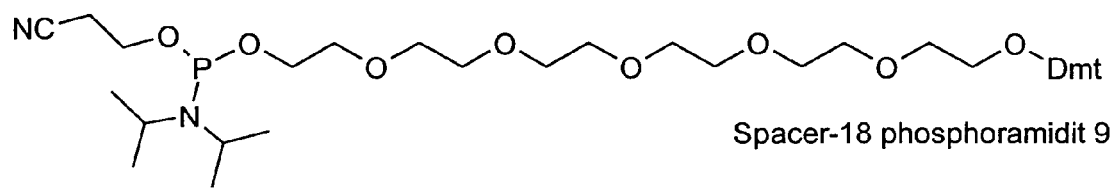
Figure 4C:
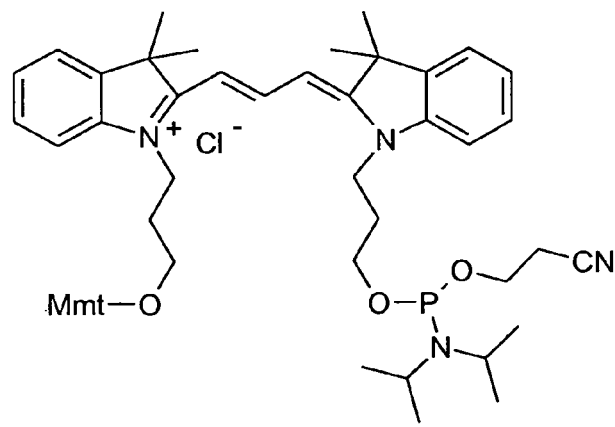
Figure 4C:
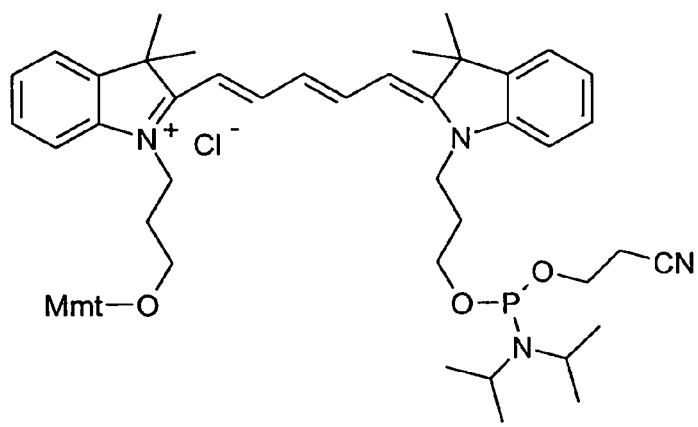
Figure 4D:
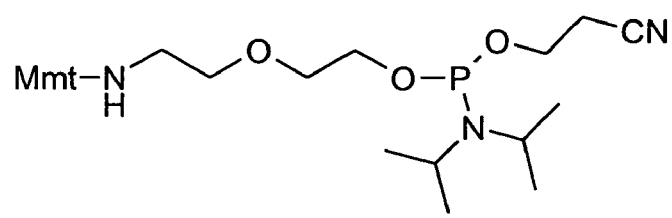
Figure 4D:
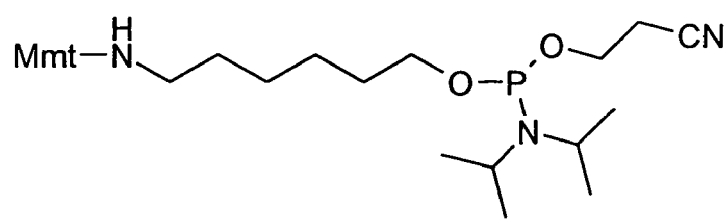

The preparation was effected, in a 0.51 µmol synthesis, in an analogous manner to that described in Example 9, with a hydroxyethylglycine-based building block having thymine as the nucleobase being coupled on in the last cycle. The hexadecyl residue was introduced with C16-phosphorylating reagent 7 (FIG. 4c). After cleaving with ammonia, 58 OD of crude product was obtained. The crude product (30 OD) was purified by electrophoresis through a 12% PAA gel. 2 OD was obtained with the expected molecular weight (caic. 3349.4; found 3349.7).

Example 15

Synthesizing Fluorescein-p-{t(oeg) at tcc gtc at}-hex (PNA-14)

The preparation was effected, in a 0.5 µmol synthesis, in an analogous manner to that described in Example 9, with a hydroxyethylglycine-based building block having thymine as the nucleobase being coupled on in the last cycle. The fluorescein residue was introduced with fluorescein-phosphoramidite 3 (FIG. 4a). After cleaving with ammonia, 62 OD of crude product was obtained. The crude product (30 OD) was purified by electrophoresis through a 12% PAA gel.

4.2 OD was obtained. The product was analyzed by negative ion mass spectrometry, which confirmed the calculated mass (calc. 3581.5; found 3582.4).

Example 16

Synthesizing HO-spacer9-p-{g(oeg)-tt agg gtt ag}-hex (PNA-15)

The preparation was effected, in a 1 µmol synthesis, in an analogous manner to that described in Example 9, with a hydroxyethylglycine-based building block having thymine as the nucleobase being coupled on in the last cycle. Spacer-9 was introduced with the corresponding phosphoramidite 8 (FIG. 4c). After cleaving with ammonia, 52 OD of crude product was obtained. The crude product (30 OD) was purified by electrophoresis through a 15% PAA gel. 1.8 OD was obtained. The product was analyzed by negative ion mass spectrometry, which confirmed the calculated mass (calc. 3402.3; found 3401.8).

Example 17

Synthesizing Lexitropsin-aminolinkC5-p-spacerC18-p-spacerC18-p-{c(oeg)-c cct tcc}-hex (PNA-16; wherein c is a pseudo-iso-cytosine PNA building block)

The preparation was effected, in a 1 µmol synthesis, in an analogous manner to that described in Example 9, with a hydroxyethylglycine-based building block having cytosine as the nucleobase being coupled on in the last cycle. After that, spacer-18 phosphoramidite 9 was condensed on, twice in succession, and amino modifier-5 phosphoramidite 12 (FIG. 4d) was then condensed on once. After the coupling reactions, the Dmt and/or Mmt group was, in each case, eliminated by treating with 3% trichloroacetic acid. In order to couple on the lexitropsin, 300 µl of the corresponding active ester (prepared from 0.1 M lexitropsincarboxylic acid, 0.1 M TBTU and 0.4 M diisopropylethylamine; 1:1:1=v:v:v; 30 min preactivation) was added and the mixture was left to react for 3 hours. Washing was then effected using DMF. After cleaving with ammonia, 43 OD of crude product was obtained. The crude product (35 OD) was purified by electrophoresis through a 15% PAA gel. 5.3 OD was obtained. The product was analyzed by negative ion mass spectrometry, which confirmed the calculated mass (calc. 3583.5; found 3583.1).

Example 18

Determining the Melting Temperatures

The melting temperatures were determined using an HP 8452A diode-array spectrophotometer, an HP 89090A Peltier element, and HP Temperature Control Software Rev. B5.1 (from Hewlett Packard). Measurements were taken in 0.5° C./min steps in 140 mM KCl, 10 mM sodium dihydrogen phosphate, 0.1 mM EDTA (pH 7.4) as the buffer. The oligomer concentration was from 0.5 to 1 $OD_{260}$ per ml.

Surprisingly, the phosphoryl-modified PNA-6 and PNA-12 to PNA-14 derivatives exhibited a higher degree of binding towards complementary DNA and RNA than did the uncharged PNA (reference substance).

| PNA derivative | | $T_m$ (DNA) | $T_m$ (RNA) |
|---|---|---|---|
| Reference | Ac-HN-tat tcc gtc at-hex | 41.9° C. | 56.6° C. |
| PNA-6 | p-{t(oeg)-at tcc gtc at}-hex | 44.0° C. | 57.5° C. |
| PNA-13 | Hexadecyl-O-p-{t(oeg) at tcc gtc at}-hex | 46.7° C. | 58.9° C. |
| PNA-14 | Fluorescein-p-{t(oeg) at tcc gtc at}-hex | 42.5° C. | 56.7° C. |
| PNA-12 | Biotin-p-{t(oeg) at tcc gtc at}-hex | 43.6° C. | 57.9° C. |

Example 19

Determining Cell Uptake After Fluorescence Labeling

COS cells were allowed to grow to confluence in Dulbecco's MEM (DMEM), which had been supplemented with 10% FCS, in 5 cm Petri dishes. The cells were washed twice with serum-free DMEM. An area of approx. 1 cm² was scratched out in the middle of the Petri dish using a sterile needle. The PNA solution (10 μM) under investigation was applied in this area. The dish was incubated at 37° C. under a $CO_2$ atmosphere. After 2, 4, and 16 hours, the cells were examined by fluorescence microscopy. For this, the cells were washed four times with serum-free DMEM, covered with a cover slip, and evaluated under the fluorescence microscope or by phase contrast.

In order to investigate the cell uptake, PNA-6 and PNA-13 were labeled as indicated directly below with fluorescein at the C terminus and then examined microscopically.

p-{t(oeg)-at tcc gtc at}-fluorescein hexadecyl-O-p-{t(oeg) at tcc gtc at}-fluorescein In this connection, it was found that the hexadecyl-PNA derivative (PNA-13) was taken up more efficiently into the cells.

Example 20

Inhibiting Cell Proliferation with PNA-13

The sequence of PNA-13 is directed against the translation start of the Ha-ras mRNA. REH cells (human pre-B leukemia cells, DSM ACC 22) or A549 tumor cells were cultured, at 37° C. and under 5% $CO_2$, in OptiMEM (Gibco BRL) containing 10% fetal calf serum (FCS, GIBCO-BRL). The cell density for the assay was approx. 1×10⁶/ml. The PNA-13 (10 μM) was incubated with the cells in 24-well plates. After incubating at 37° C. and under 5% $CO_2$ for 96 hours, the cell density was determined. Mean values for the cell density were determined from 3 individual wells at a given PNA concentration. It was found that PNA-13 inhibits proliferation of the REH cells. After >4 days of incubation, the inhibition brought about by PNA-13 was greater than that brought about by a corresponding phosphorothioate oligonucleotide.

Example 21

Synthesizing HO-spacer9-p-{gtt agg gtt ag}-hex (PNA-17)

The preparation was effected, in a 0.67 μmol synthesis, in an analogous manner to that described in Examples 9 and 16, with a normal 2-aminoethylglycine building block, having thymine as the nucleobase, being coupled on in the last cycle of the PNA synthesis. Spacer-9 was subsequently introduced using the corresponding phosphoramidite 8 (FIG. 4c) (3×5 min reaction time). After cleaving with ammonia, 108 OD of crude product was obtained. The crude product was purified by electrophoresis through a 15% PAA gel. 5.7 OD was obtained. The product was analyzed by negative ion mass spectrometry, which confirmed the calculated mass (calc. 3401.3; found 3399.8).

Example 22

Synthesizing Thiophosphate-{t(oeg)-at tcc gtc at}-hex (PNA-18)

The preparation was effected, in a 1 μmol synthesis, in an analogous manner to that described in Examples 2 and 7, with a hydroxyethylglycine-based building block having thymine as the nucleobase being coupled on in the last cycle. After eliminating the terminal Dmt group with 3% TCA, the free hydroxyl function was reacted with phosphorylating reagent 1 (FIG. 4a) using tetrazole as catalyst. After the condensation was complete, oxidation was effected using the Beaucage reagent (0.075 M 3H-1,2-benzodithiol-3-one 1,1-dioxide in acetonitrile) in order to introduce the thio function. After cleaving with ammonia, 66.5 OD of crude product was obtained. 61 OD of the crude product was purified by electrophoresis through a 15% PAA gel. 12.4 OD was obtained. The product was analyzed by negative ion mass spectrometry, which confirmed the calculated mass (calc. 3141; found 3140).

List of abbreviations:
ACN acetonitrile
BOC tert-butyloxycarbonyl
C, c pseudo-iso-cytosine
COS CV1 origin SV 40
CPG controlled pore glass
DCM dichloromethane
DIPEA diisopropylethylamine
DMEM Dulbecco's MEM
DMF dimethylformamide
Dmt dimethoxytrityl
DNA deoxyribonucleic acid
DNP dinitroaryl
FITC fluorescein isothiocyanate
Fmoc fluorenylmethoxycarbonyl
HATU O-(7-azabenzotriazol-1-yl)-1,1,3,3-tetramethyluronium hexafluorophosphate
HBTU O-(benzotriazol-1-yl)-1,1,3,3-tetramethyluronium hexafluorophosphate
hex —NH—$(CH_2)_6$—OH
MEM modified Eagle's minimal essential medium
Mmt monomethoxytrityl
OD optical density
oeg N-(2-hydroxyethyl)glycine
PAA polyacrylamide PG protecting group
PNA polyamide nucleic acid
RNA ribonucleic acid
TBTU O-(benzotriazol-1-yl)-1,1,3,3-tetramethyluronium tetrafluoroborate
TCA trichloroacetic acid
THF tetrahydrofuran
TR acid-labile protecting group All references cited herein are hereby incorporated in their entirety by reference.

What is claimed is:

1. A process for preparing a PNA derivative of Formula I

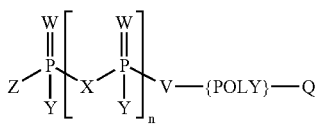

Formula I wherein

V is oxygen, sulfur, $NR_1$, $U-(CR_3R_4)_{u'}-CH_2-C(O)-NH$ or $U-(CH_2CH_2O)_{u'}-C(O)-NH$;

U is, independently of any other U, oxygen, sulfur or NH;

u' is, independently of any other u', from 1 to 10;

W is, independently of any other W, oxygen, sulfur or $NR_1$;

Y is, independently of any other Y, hydroxyl, mercapto, oxyanion, thioate or $NR_1R_2$;

$R_1$ and $R_2$ are, independently of each other, a radical consisting of hydrogen or $C_1$-$C_6$-alkyl;

$R_3$ and $R_4$ are, independently of each other, a radical consisting of hydrogen or $C_1$-$C_6$-alkyl, or the radical of an amino acid side chain;

X is, independently of any other X,
    $U-(C_2$-$C_{22}$-alkanediyl)-U,
    $U-(CH_2CH_2O)_{u'}$,
    a bifunctional labeling group,
    a bifunctional group for crosslinking with complementary nucleic acids,
    a bifunctional group which promotes intracellular uptake, or
    a bifunctional group which increases the binding affinity of the PNA derivative for a
    target nucleic acid;

Z is hydroxyl,
    mercapto,
    oxyanion,
    thioate,
    $NR_1R_2$,
    $C_1$-$C_{22}$-alkyl,
    $C_1$-$C_8$-arylalkyl,
    $C_1$-$C_{22}$-alkyl-U,
    $C_1$-$C_8$-arylalkyl-U,
    hydroxy-$C_1$-$C_{18}$-U,
    aminoalkyl-U,
    arylalkyl-U,
    mercaptoalkyl-U,
    a group of the formula $R_9(CH_2CH_2-O)_m$, wherein $R_9$ is hydroxyl, amino or $C_1$-$C_{22}$-alkoxy,
    and m is from 1 to 100,
    a monofunctional or bifunctional labeling group,
    a monofunctional or bifunctional crosslinking group,
    a monofunctional or bifunctional group which promotes intracellular uptake, or
    a monofunctional or bifunctional group which promotes the binding affinity of the
    PNA derivative for a target nucleic acid;

n is from 0 to 10;

Q is hydroxyl, amino, $NHR_7$, $NR_7R_8$, an amino acid derivative or a peptide radical;

$R_7$ and $R_8$ are, independently of each other, $C_1$-$C_{18}$-alkyl or hydroxy-$C_1$-$C_{18}$-alkyl;

and wherein {POLY} is described by the Formula II

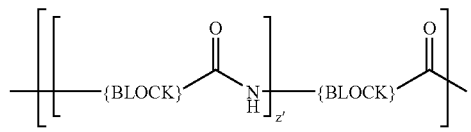

Formula II wherein {BLOCK} is, independently of any other {BLOCK}, described by Formula IIIA,

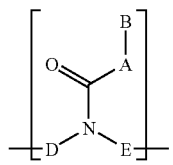

Formula IIIA

Formula IIIB,

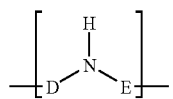

Formula IIIB or Formulae IV A to IV G,

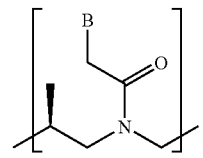

Formula IV A

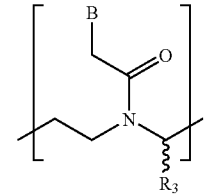

Formula IV B

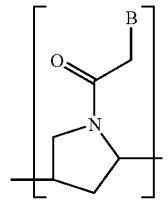

Formula IV C

Formula IV D

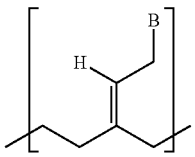

Formula IV E

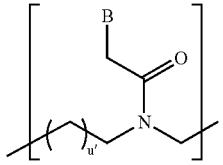

Formula IV F

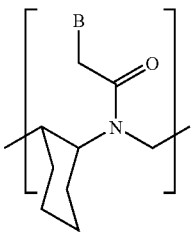

Formula IV G wherein each building block {BLOCK} can be different, and wherein z' is from 0 to 100;

A is, independently of any other A, $(CR_1R_2)_s$, wherein s is from 1 to 3;

B is, independently of any other B,
an aromatic radical, which optionally possesses heteroaromatic character,
hydrogen,
hydroxyl,
$C_1$-$C_{18}$-alkyl,
or a nucleobase or its prodrug form,
wherein at least one B radical is a nucleobase;

D is, independently of any other D, $(CR_3R_4)_t$, wherein t is from 2 to 10,
wherein two adjacent $R_3$ and $R_4$ radicals can form a $C_5$-$C_8$-cycloalkyl ring, E is, independently of any other E, $(CR_5R_6)_{u'}$, $R_5$ and $R_6$ are, independently of each other, a radical consisting of hydrogen or $C_1$-$C_6$-alkyl,
or an amino acid side chain, wherein two adjacent $R_5$ and $R_6$ radicals
can form a $C_5$-$C_8$-cycloalkyl ring or a spiro compound, and wherein $R_1$, $R_2$, $R_3$, $R_4$ and u' are as defined above;

and physiologically tolerated salts of the PNA derivative of the Formula I, with the proviso that at least one Y or Z radical is hydroxyl, mercapto, oxyanion or thioate;

wherein said process comprises
a) synthesizing a backbone for the PNA derivative, starting from the C terminus, by sequentially coupling with amidonucleic acid monomers, which are optionally N-terminally protected;
b) optionally deprotecting the N-terminally protected PNA backbone;

c) coupling a phosphorus (III) or a phosphorus (V) group to the N-terminus of the PNA backbone, using activated phosphorylating reagents optionally containing a spacer;
d) optionally repeating step c); and
e) optionally oxidizing the phosphorus (III) group to a phosphorus (V) group.

2. The process as claimed in claim 1, wherein the PNA is prepared using t-butyloxycarbonyl (BOG), 9-fluorenyl-methoxycarbonyl (Fmoc), or monomethoxytrityl (Mmt) protecting groups.

3. The process as claimed in claim 2, wherein the PNA is prepared using solid supports.

4. The process as claimed in claim 3, wherein CPG, tentagel, or aminomethylpolystyrene is used as the solid support.

5. The process as claimed in claim 1, further comprising purifying the PNA derivative using chromatography or electrophoresis.

6. The process as claimed in claim 5, wherein the PNA derivative is purified using chromatography using a basic stationary phase and an acid or salt-containing eluent.

7. The process as claimed in claim 6, wherein the stationary phase is an anion exchanger or a mixed-mode phase.

* * * * *